(12) United States Patent
Albrecht et al.

(10) Patent No.: US 8,313,431 B2
(45) Date of Patent: Nov. 20, 2012

(54) SPLIT HOOP WOUND RETRACTOR

(75) Inventors: Jeremy J. Albrecht, Rancho Santa Margarita, CA (US); Charles C. Hart, Summerville, SC (US); John R. Brustad, Dana Point, CA (US); Gary M. Johnson, Mission Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 239 days.

(21) Appl. No.: 12/905,932

(22) Filed: Oct. 15, 2010

(65) Prior Publication Data
US 2011/0060193 A1 Mar. 10, 2011

Related U.S. Application Data

(63) Continuation of application No. 11/548,765, filed on Oct. 12, 2006, now Pat. No. 7,815,567.

(60) Provisional application No. 60/726,826, filed on Oct. 14, 2005, provisional application No. 60/745,730, filed on Apr. 26, 2006, provisional application No. 60/803,346, filed on May 26, 2006, provisional application No. 60/803,965, filed on Jun. 5, 2006, provisional application No. 60/828,089, filed on Oct. 4, 2006.

(51) Int. Cl.
*A61B 1/32* (2006.01)
(52) U.S. Cl. .................. 600/208; 600/206; 600/215
(58) Field of Classification Search .................. 606/108; 600/21, 22, 201, 203, 206–208, 215, 225, 600/231
See application file for complete search history.

(56) References Cited

U.S. PATENT DOCUMENTS

| 558,364 A | 4/1896 | Doolittle |
|---|---|---|
| 1,157,202 A | 10/1915 | Bates et al. |
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |

(Continued)

FOREIGN PATENT DOCUMENTS
DE 26 05 148 A1 8/1977
(Continued)

OTHER PUBLICATIONS

U.S. Appl. No. 10/902,756, filed Jul. 29, 2004; Title: Hand Access Port Device, now abandoned.

(Continued)

*Primary Examiner* — Alvin Stewart
*Assistant Examiner* — Christina Negrellirodriguez
(74) *Attorney, Agent, or Firm* — Patrick Y. Ikehara

(57) ABSTRACT

An incrementally adjustable wound retractor, which provides access to a body cavity, includes an inner ring having a diameter greater than the desired diameter of the wound incision, an outer ring having an annular axis and a diameter greater than the desired diameter of the wound incision, and a flexible sleeve disposed in a generally cylindrical form between the inner and outer rings. The outer ring includes first and second circular tubes spaced apart axially with each including a lumen having a rigid, noncompliant split hoop placed therein. The outer ring may be rolled over itself and around the annular axis to retract the sleeve with sufficient force to stretch the incision to the desired diameter. A gel cap seal may be coupled to the outer ring outside of the biological body to seal the opening produced by the wound retractor between the body cavity and outside the body cavity.

20 Claims, 12 Drawing Sheets

U.S. PATENT DOCUMENTS

| | | |
|---|---|---|
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Benjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter et al. |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier et al. |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |

| | | | | | |
|---|---|---|---|---|---|
| 5,104,389 A | 4/1992 | Deem | 5,366,478 A | 11/1994 | Brinkerhoff et al. |
| 5,125,396 A | 6/1992 | Ray | 5,368,545 A | 11/1994 | Schaller et al. |
| 5,125,897 A | 6/1992 | Quinn et al. | 5,375,588 A | 12/1994 | Yoon |
| 5,127,626 A | 7/1992 | Hilal et al. | 5,380,288 A | 1/1995 | Hart et al. |
| 5,129,885 A | 7/1992 | Green et al. | 5,383,861 A | 1/1995 | Hempel et al. |
| 5,141,498 A | 8/1992 | Christian | 5,385,552 A | 1/1995 | Haber et al. |
| 5,149,327 A | 9/1992 | Oshiyama | 5,385,553 A | 1/1995 | Hart et al. |
| 5,156,617 A | 10/1992 | Reid | 5,385,560 A | 1/1995 | Wulf |
| 5,158,553 A | 10/1992 | Berry et al. | 5,389,080 A | 2/1995 | Yoon |
| 5,159,921 A | 11/1992 | Hoover | 5,389,081 A | 2/1995 | Castro |
| 5,161,773 A | 11/1992 | Tower | 5,391,153 A | 2/1995 | Haber et al. |
| 5,167,636 A | 12/1992 | Clement | 5,391,156 A | 2/1995 | Hildwein et al. |
| 5,167,637 A | 12/1992 | Okada et al. | 5,395,367 A | 3/1995 | Wilk |
| 5,176,648 A | 1/1993 | Holmes et al. | 5,403,264 A | 4/1995 | Wohlers et al. |
| 5,176,662 A | 1/1993 | Bartholomew et al. | 5,403,336 A | 4/1995 | Kieturakis et al. |
| 5,176,697 A | 1/1993 | Hasson et al. | 5,407,433 A | 4/1995 | Loomas |
| 5,178,162 A | 1/1993 | Bose | 5,411,483 A | 5/1995 | Loomas |
| 5,180,365 A | 1/1993 | Ensminger et al. | 5,413,571 A | 5/1995 | Katsaros et al. |
| 5,183,471 A | 2/1993 | Wilk | 5,423,848 A | 6/1995 | Washizuka et al. |
| 5,188,595 A | 2/1993 | Jacobi | 5,429,609 A | 7/1995 | Yoon |
| 5,188,607 A | 2/1993 | Wu | 5,431,676 A | 7/1995 | Dubrul et al. |
| 5,192,301 A | 3/1993 | Kamiya et al. | 5,437,683 A | 8/1995 | Neumann et al. |
| 5,197,955 A | 3/1993 | Stephens et al. | 5,439,455 A | 8/1995 | Kieturakis et al. |
| 5,201,714 A | 4/1993 | Gentelia et al. | 5,441,486 A | 8/1995 | Yoon |
| 5,207,656 A | 5/1993 | Kranys | 5,443,452 A | 8/1995 | Hart et al. |
| 5,209,737 A | 5/1993 | Ritchart et al. | 5,456,284 A | 10/1995 | Ryan et al. |
| 5,211,370 A | 5/1993 | Powers | 5,460,170 A | 10/1995 | Hammerslag |
| 5,211,633 A | 5/1993 | Stouder, Jr. | 5,460,616 A | 10/1995 | Weinstein et al. |
| 5,213,114 A | 5/1993 | Bailey, Jr. | 5,468,248 A | 11/1995 | Chin et al. |
| 5,226,890 A | 7/1993 | Ianniruberto et al. | 5,476,475 A | 12/1995 | Gadberry |
| 5,234,455 A | 8/1993 | Mulhollan | 5,480,410 A | 1/1996 | Cuschieri et al. |
| 5,241,968 A | 9/1993 | Slater | 5,486,426 A | 1/1996 | McGee et al. |
| 5,242,409 A | 9/1993 | Buelna | 5,490,843 A | 2/1996 | Hildwein et al. |
| 5,242,412 A | 9/1993 | Blake, III | 5,492,304 A | 2/1996 | Smith et al. |
| 5,242,415 A | 9/1993 | Kantrowitz et al. | 5,496,280 A | 3/1996 | Vandenbroek et al. |
| 5,248,304 A | 9/1993 | Vigdorchik et al. | 5,503,112 A | 4/1996 | Luhman et al. |
| 5,256,150 A | 10/1993 | Quiachon et al. | 5,507,758 A | 4/1996 | Thomason et al. |
| 5,257,973 A | 11/1993 | Villasuso | 5,508,334 A | 4/1996 | Chen |
| 5,257,975 A | 11/1993 | Foshee | 5,511,564 A | 4/1996 | Wilk |
| 5,259,366 A | 11/1993 | Reydel et al. | 5,514,109 A | 5/1996 | Mollenauer et al. |
| 5,261,883 A | 11/1993 | Hood et al. | 5,514,133 A | 5/1996 | Golub et al. |
| 5,262,468 A | 11/1993 | Chen | 5,514,153 A | 5/1996 | Bonutti |
| 5,263,922 A | 11/1993 | Sova et al. | 5,518,278 A | 5/1996 | Sampson |
| 5,269,763 A | 12/1993 | Boehmer et al. | 5,520,632 A | 5/1996 | Leveen |
| 5,269,772 A | 12/1993 | Wilk | 5,522,791 A | 6/1996 | Leyva |
| 5,273,449 A | 12/1993 | Mattis et al. | 5,522,824 A | 6/1996 | Ashby |
| 5,273,545 A | 12/1993 | Hunt et al. | 5,524,644 A | 6/1996 | Crook |
| D343,236 S | 1/1994 | Quigley et al. | 5,526,536 A | 6/1996 | Cartmill |
| 5,279,575 A | 1/1994 | Sugarbaker | 5,531,758 A | 7/1996 | Uschold et al. |
| 5,290,310 A | 3/1994 | Makower et al. | 5,538,509 A | 7/1996 | Dunlap et al. |
| D346,022 S | 4/1994 | Quigley et al. | 5,540,648 A | 7/1996 | Yoon |
| 5,299,582 A | 4/1994 | Potts | 5,540,711 A | 7/1996 | Kieturakis et al. |
| 5,300,034 A | 4/1994 | Behnke | 5,545,150 A | 8/1996 | Danks et al. |
| 5,300,035 A | 4/1994 | Clement | 5,545,179 A | 8/1996 | Williamson, IV |
| 5,300,036 A | 4/1994 | Mueller et al. | 5,549,563 A | 8/1996 | Kronner |
| 5,308,336 A | 5/1994 | Hart et al. | 5,549,637 A | 8/1996 | Crainich |
| 5,309,896 A | 5/1994 | Moll et al. | 5,554,124 A | 9/1996 | Alvarado |
| 5,312,391 A | 5/1994 | Wilk | 5,562,632 A | 10/1996 | Davila et al. |
| 5,314,417 A | 5/1994 | Stephens et al. | 5,562,677 A | 10/1996 | Hildwein et al. |
| 5,316,541 A | 5/1994 | Fischer | 5,562,688 A | 10/1996 | Riza |
| 5,320,611 A | 6/1994 | Bonutti et al. | 5,571,115 A | 11/1996 | Nicholas |
| 5,330,437 A | 7/1994 | Durman | 5,571,137 A | 11/1996 | Marlow et al. |
| 5,330,486 A | 7/1994 | Wilk | 5,575,799 A | 11/1996 | Bolanos et al. |
| 5,330,497 A | 7/1994 | Freitas et al. | 5,577,993 A | 11/1996 | Zhu et al. |
| 5,331,975 A | 7/1994 | Bonutti | 5,578,048 A | 11/1996 | Pasqualucci et al. |
| 5,334,143 A | 8/1994 | Carroll | 5,580,344 A | 12/1996 | Hasson |
| 5,334,646 A | 8/1994 | Chen | 5,584,850 A | 12/1996 | Hart et al. |
| 5,336,192 A | 8/1994 | Palestrant | 5,601,579 A | 2/1997 | Semertzides |
| 5,336,708 A | 8/1994 | Chen | 5,601,581 A | 2/1997 | Fogarty et al. |
| 5,338,313 A | 8/1994 | Mollenauer et al. | 5,603,702 A | 2/1997 | Smith et al. |
| 5,342,315 A | 8/1994 | Rowe et al. | 5,607,443 A | 3/1997 | Kieturakis et al. |
| 5,342,385 A | 8/1994 | Norelli et al. | 5,620,415 A | 4/1997 | Lucey et al. |
| 5,350,364 A | 9/1994 | Stephens et al. | 5,620,420 A | 4/1997 | Kriesel |
| 5,353,786 A | 10/1994 | Wilk | 5,628,732 A | 5/1997 | Antoon, Jr. et al. |
| 5,354,280 A | 10/1994 | Haber et al. | 5,632,284 A | 5/1997 | Graether |
| 5,360,417 A | 11/1994 | Gravener et al. | 5,632,979 A | 5/1997 | Goldberg et al. |
| 5,364,345 A | 11/1994 | Lowery et al. | 5,634,911 A | 6/1997 | Hermann et al. |
| 5,364,372 A | 11/1994 | Danks et al. | 5,634,936 A | 6/1997 | Linden et al. |
| 5,366,446 A | 11/1994 | Tal et al. | 5,634,937 A | 6/1997 | Mollenauer et al. |

| Patent | Date | Name |
|---|---|---|
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |
| 5,657,963 A | 8/1997 | Hinchliffe et al. |
| 5,658,272 A | 8/1997 | Hasson |
| 5,658,306 A | 8/1997 | Kieturakis et al. |
| 5,662,615 A | 9/1997 | Blake, III |
| 5,672,168 A | 9/1997 | de la Torre et al. |
| 5,681,341 A | 10/1997 | Lunsford et al. |
| 5,683,378 A | 11/1997 | Christy |
| 5,685,854 A | 11/1997 | Green et al. |
| 5,685,857 A | 11/1997 | Negus et al. |
| 5,697,914 A | 12/1997 | Brimhall |
| 5,707,703 A | 1/1998 | Rothrum et al. |
| 5,709,664 A | 1/1998 | Vandenbroek et al. |
| 5,713,858 A | 2/1998 | Heruth et al. |
| 5,713,869 A | 2/1998 | Morejon |
| 5,720,730 A | 2/1998 | Blake, III |
| 5,725,536 A | 3/1998 | Oberlin et al. |
| 5,728,103 A | 3/1998 | Picha et al. |
| 5,730,748 A | 3/1998 | Fogarty et al. |
| 5,735,791 A | 4/1998 | Alexander et al. |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,753,150 A | 5/1998 | Martin et al. |
| 5,755,660 A | 5/1998 | Tyagi |
| 5,760,117 A | 6/1998 | Chen |
| 5,769,783 A | 6/1998 | Fowler |
| 5,782,812 A | 7/1998 | Hart et al. |
| 5,782,817 A | 7/1998 | Franzel et al. |
| 5,782,859 A | 7/1998 | Nicholas et al. |
| 5,788,676 A | 8/1998 | Yoon |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,803,923 A | 9/1998 | Singh-Derewa et al. |
| 5,807,350 A | 9/1998 | Diaz |
| 5,810,712 A | 9/1998 | Dunn |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom et al. |
| 5,819,375 A | 10/1998 | Kastner |
| 5,820,555 A | 10/1998 | Watkins, III et al. |
| 5,820,600 A | 10/1998 | Carlson et al. |
| 5,830,191 A | 11/1998 | Hildwein et al. |
| 5,832,925 A | 11/1998 | Rothrum |
| 5,836,871 A | 11/1998 | Wallace et al. |
| 5,841,298 A | 11/1998 | Huang |
| 5,842,971 A | 12/1998 | Yoon |
| 5,848,992 A | 12/1998 | Hart et al. |
| 5,853,395 A | 12/1998 | Crook et al. |
| 5,853,417 A | 12/1998 | Fogarty et al. |
| 5,857,461 A | 1/1999 | Levitsky et al. |
| 5,860,995 A | 1/1999 | Berkelaar |
| 5,865,728 A | 2/1999 | Moll et al. |
| 5,865,729 A | 2/1999 | Meehan et al. |
| 5,865,807 A | 2/1999 | Blake, III |
| 5,865,817 A | 2/1999 | Moenning et al. |
| 5,871,474 A | 2/1999 | Hermann et al. |
| 5,876,413 A | 3/1999 | Fogarty et al. |
| 5,879,368 A | 3/1999 | Hoskin et al. |
| 5,882,344 A | 3/1999 | Stouder, Jr. |
| 5,884,639 A | 3/1999 | Chen |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,913,847 A | 6/1999 | Yoon |
| 5,916,198 A | 6/1999 | Dillow |
| 5,916,232 A | 6/1999 | Hart |
| 5,919,476 A | 7/1999 | Fischer et al. |
| 5,931,832 A | 8/1999 | Jensen |
| 5,947,922 A | 9/1999 | MacLeod |
| 5,951,467 A | 9/1999 | Picha et al. |
| 5,951,588 A | 9/1999 | Moenning |
| 5,957,888 A | 9/1999 | Hinchliffe |
| 5,957,913 A | 9/1999 | de la Torre et al. |
| 5,962,572 A | 10/1999 | Chen |
| 5,964,781 A | 10/1999 | Mollenauer et al. |
| 5,976,174 A | 11/1999 | Ruiz |
| 5,989,232 A | 11/1999 | Yoon |
| 5,989,233 A | 11/1999 | Yoon |
| 5,989,266 A | 11/1999 | Foster |
| 5,993,471 A | 11/1999 | Riza et al. |
| 5,993,485 A | 11/1999 | Beckers |
| 5,994,450 A | 11/1999 | Pearce |
| 5,997,515 A | 12/1999 | de la Torre et al. |
| 6,004,303 A | 12/1999 | Peterson |
| 6,010,494 A | 1/2000 | Schafer et al. |
| 6,017,355 A | 1/2000 | Hessel et al. |
| 6,018,094 A | 1/2000 | Fox |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,042,573 A | 3/2000 | Lucey |
| 6,045,535 A | 4/2000 | Ben Nun |
| 6,048,309 A | 4/2000 | Flom et al. |
| 6,050,871 A | 4/2000 | Chen |
| 6,053,934 A | 4/2000 | Andrews et al. |
| 6,059,816 A | 5/2000 | Moenning |
| 6,066,117 A | 5/2000 | Fox et al. |
| 6,068,639 A | 5/2000 | Fogarty et al. |
| 6,077,288 A | 6/2000 | Shimomura |
| 6,086,603 A | 7/2000 | Termin et al. |
| 6,090,043 A | 7/2000 | Austin et al. |
| 6,099,506 A | 8/2000 | Macoviak et al. |
| 6,110,154 A | 8/2000 | Shimomura et al. |
| 6,123,689 A | 9/2000 | To |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,197,002 B1 | 3/2001 | Peterson |
| 6,217,555 B1 | 4/2001 | Hart et al. |
| 6,217,590 B1 | 4/2001 | Levinson |
| 6,224,612 B1 | 5/2001 | Bates et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,533 B1 | 7/2001 | Fadem et al. |
| 6,254,534 B1 | 7/2001 | Butler et al. |
| 6,258,065 B1 | 7/2001 | Dennis et al. |
| 6,264,604 B1 | 7/2001 | Kieturakis et al. |
| 6,267,751 B1 | 7/2001 | Mangosong |
| 6,276,661 B1 | 8/2001 | Laird |
| 6,287,280 B1 | 9/2001 | Lampropoulos et al. |
| 6,315,770 B1 | 11/2001 | de la Torre et al. |
| 6,319,246 B1 | 11/2001 | de la Torre et al. |
| 6,322,541 B2 | 11/2001 | West |
| 6,325,384 B1 | 12/2001 | Berry, Sr. et al. |
| 6,346,074 B1 | 2/2002 | Roth |
| 6,371,968 B1 | 4/2002 | Kogasaka et al. |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,420,475 B1 | 7/2002 | Chen |

| | | |
|---|---|---|
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Lui et al. |
| 7,105,009 B2 | 9/2006 | Johnson |
| 7,105,607 B2 | 9/2006 | Chen |
| 7,108,009 B2 | 9/2006 | Ishida |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,850,667 B2 | 12/2010 | Gresham |
| 7,867,164 B2 | 1/2011 | Butler et al. |
| 7,878,974 B2 | 2/2011 | Brustad et al. |
| 7,883,461 B2 | 2/2011 | Albrecht et al. |

| | | |
|---|---|---|
| 7,892,172 B2 | 2/2011 | Albrecht et al. |
| 7,896,889 B2 | 3/2011 | Mazzocchi et al. |
| 7,909,760 B2 | 3/2011 | Albrecht et al. |
| 7,913,697 B2 | 3/2011 | Nguyen et al. |
| 7,930,782 B2 | 4/2011 | Chen |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0004253 A1 | 1/2003 | Chen |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 | 2/2005 | Ahlberg et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0090713 A1 | 4/2005 | Gozales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0118175 A1 | 5/2007 | Butler et al. |
| 2007/0151566 A1 | 7/2007 | Kahle et al. |
| 2007/0156023 A1 | 7/2007 | Frasier et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegel et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |
| 2010/0261975 A1 | 10/2010 | Huey et al. |
| 2010/0286484 A1 | 11/2010 | Stellon et al. |

| | | | |
|---|---|---|---|
| 2010/0298646 A1 | 11/2010 | Stellon et al. | |
| 2011/0021877 A1 | 1/2011 | Fortier et al. | |
| 2011/0028891 A1 | 2/2011 | Okoniewski | |
| 2011/0034935 A1 | 2/2011 | Kleyman | |
| 2011/0034946 A1 | 2/2011 | Kleyman | |
| 2011/0034947 A1 | 2/2011 | Kleyman | |
| 2011/0071462 A1 | 3/2011 | Ewers et al. | |
| 2011/0071463 A1 | 3/2011 | Ewers et al. | |

FOREIGN PATENT DOCUMENTS

| | | |
|---|---|---|
| DE | 33 36 279 C2 | 1/1986 |
| DE | 37 39 532 | 12/1988 |
| DE | 37 37 121 | 5/1989 |
| DE | 296 00 939 | 6/1996 |
| DE | 19828009 | 12/1999 |
| EP | 0113520 | 7/1984 |
| EP | 0142262 | 5/1985 |
| EP | 0 517 248 | 12/1992 |
| EP | 0537768 | 4/1993 |
| EP | 0 807 416 | 11/1997 |
| EP | 0 849 517 | 6/1998 |
| EP | 0950376 | 10/1999 |
| EP | 1118657 | 7/2001 |
| EP | 1 125 552 | 8/2001 |
| EP | 1312318 | 5/2003 |
| EP | 1 407 715 | 4/2004 |
| EP | 2044889 | 4/2009 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| SU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO95/07056 | 3/1995 |
| WO | WO 95/07056 | 3/1995 |
| WO | WO 95/22289 | 8/1995 |
| WO | WO95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO00/32116 | 6/2000 |
| WO | WO 00/32119 | 6/2000 |
| WO | WO 00/32120 | 6/2000 |
| WO | WO 00/35356 | 6/2000 |
| WO | WO 00/32120 | 8/2000 |
| WO | WO00/54675 | 9/2000 |
| WO | WO 00/54675 | 9/2000 |
| WO | WO00/54676 | 9/2000 |
| WO | WO 00/54676 | 9/2000 |
| WO | WO 00/54677 | 9/2000 |
| WO | WO00/54677 | 9/2000 |
| WO | WO 01/08563 | 2/2001 |
| WO | WO 01/08581 | 2/2001 |
| WO | WO01/08581 | 2/2001 |
| WO | WO 01/26558 | 4/2001 |
| WO | WO 01/26559 | 4/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO02/34108 | 5/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO03/032819 | 4/2003 |
| WO | WO03/034908 | 5/2003 |
| WO | WO 03/034908 | 5/2003 |
| WO | WO03/061480 | 7/2003 |
| WO | WO 03/061480 | 7/2003 |
| WO | WO 03/077726 | 9/2003 |
| WO | WO 03/103548 | 12/2003 |
| WO | WO03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2008/015566 | 2/2008 |
| WO | WO 2008/093313 | 8/2008 |
| WO | WO 2008/121294 | 10/2008 |
| WO | WO 2010/082722 | 7/2010 |
| WO | WO 2010/104259 | 9/2010 |

OTHER PUBLICATIONS

U.S. Appl. No. 10/802,125; filed Mar. 15, 2004; Title: Surgical Guide Valve, now abandoned.

U.S. Appl. No. 10/927,551; filed Aug. 25, 2004; Title: Surgical Access System, now abandoned.

U.S. Appl. No. 10/695,295, filed Oct. 28, 2003; Title: Surgical Gel Seal.

U.S. Appl. No. 11/132,741, filed May 18, 2005; Title: Gas-Tight Seal Accomodating Surgical Instruments With a Wide Range of Diameters.

U.S. Appl. No. 11/245,709, filed Oct. 7, 2005; Title: Surgical Access System.
U.S. Appl. No. 11/330,661, filed Jan. 12, 2006; Title: Sealed Surgical Access Device.
U.S. Appl. No. 11/564,409, filed Nov. 29, 2006; Title: Surgical Instrument Access Device.
U.S. Appl. No. 12/108,400, filed Apr. 23, 2008; Title: Wound Retraction Apparatus and Method.
U.S. Appl. No. 12/119,371, filed May 12, 2008; Title: Surgical Retractor With Gel Pad.
U.S. Appl. No. 12/119,414, filed May 12, 2008; Title: Surgical Retractor.
U.S. Appl. No. 12/358,080, filed Jan. 22, 2009; Title: Surgical Instrument Access Device.
U.S. Appl. No. 12/360,634, filed Jan. 27, 2009; Title: Surgical Access Apparatus and Method.
U.S. Appl. No. 12/360,710, filed Jan. 27, 2009; Title: Surgical Access Apparatus and Method.
U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011.
U.S. Appl. No. 13/008,728, filed Jan. 18, 2011.
U.S. Appl. No. 13/023,334, filed Feb. 8, 2011.
U.S. Appl. No. 13/031,892, filed Feb. 22, 2011.
U.S. Appl. No. 13/050,042, filed Mar. 17, 2011.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic Instrument and Cannula Assembly and Related Surgical Method.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc.
European Patent Office, European Search Report for European Application No. EP 10 18 4681, dated Nov. 22, 2010, entitled "Wound Retraction Apparatus and Method".
European Patent Office, European Search Report for European Application No. EP 10 18 4608, dated Nov. 22, 2010, entitled "Wound Retraction Apparatus and Method".
European Patent Office, European Search Report for European Application No. EP 10 18 4648, dated Nov. 22, 2010, entitled "Wound Retraction Apparatus and Method".
European Patent Office, European Search Report for European Application No. EP 10 18 4731, dated Nov. 22, 2010, entitled "Wound Retraction Apparatus and Method".
European Patent Office, European Search Report for European Application No. EP 10 18 4661, dated Nov. 22, 2010, entitled "Wound Retraction Apparatus and Method".
European Patent Office, European Search Report for European Application No. EP 10 18 4677, dated Nov. 22, 2010, entitled "Wound Retraction Apparatus and Method".
European Patent Office, European Search Report for European Application No. EP 10 18 9325, dated Dec. 14, 2010, entitled "Split Hoop Wound Retractor".
European Patent Office, European Search Report for European Application No. EP 10 18 9327, dated Dec. 14, 2010, entitled "Split Hoop Wound Retractor".
European Patent Office, European Search Report for European Application No. EP 10 18 9328, dated Dec. 15, 2010, entitled "Split Hoop Wound Retractor".
European Patent Office, European Search Report for European Application No. EP 04 00 2888, dated Sep. 10, 2004, entitled "Hand Access Port Device".
European Patent Office, European Search Report for European Application No. EP 04 00 2889, dated Sep. 13, 2004, entitled "Hand Access Port Device".
European Patent Office, International Search Report and the Written Opinion of the International Searching Authority for International Application No. PCT/US2006/040154, mailed Jan. 30, 2007.
European Patent Office, International Search Report and the Written Opinion of the International Searching Authority for International Application No. PCT/US2006/040073, mailed Jan. 26, 2007.
European Patent Office, International Search Report and the Written Opinion of the International Searching Authority for International Application No. PCT/US2006/039905, mailed Jan. 17, 2007.
European Patent Office, International Search Report and the Written Opinion of the International Searching Authority for International Application No. PCT/US2006/039883, mailed Jan. 31, 2007.
European Patent Office, International Search Report and the Written Opinion of the International Searching Authority for International Application No. PCT/US2006/039800, mailed Apr. 16, 2007.
European Patent Office, International Search Report and the Written Opinion of the International Searching Authority for International Application No. PCT/US2006/039799, mailed Mar. 27, 2007.
European Search Report for corresponding EP 08253236 date of mailing is Feb. 10, 2009 (6 pages).
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484.
International Searching Authority/US, International Search Report and the Written Opinion of the International Searching Authority for International Application No. PCT/US01/29682.
McSweeney, Cannulation of the Rumen in Cattle and Buffaloes, Australian Veterinary Journal, Aug. 1989, vol. 66, No. 8, pp. 266-268.
Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan.
The International Bureau of WIPO, International Preliminary Report on Patentability, dated Aug. 29, 2006, for International Application No. PCT/US2004/028250.

The International Bureau of WIPO, International Preliminary Report on Patentability, dated Apr. 16, 2008, for International Application No. PCT/US2006/039799.
The International Bureau of WIPO, International Preliminary Report on Patentability for International Application No. PCT/US2006/039800 dated Apr. 16, 2008.
Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.
Kagaya, Laparascopic cholecystecomy via two ports, using the "Twin-Port" system, J. Hepatobiliary Pancreat Surg (2001) 8:76-80.
International Search Report and Written Opinion in PCT/IE2005/000113 mailed on Feb. 22, 2006.
International Search Report and Written Opinion in PCT/IE2007/000050 mailed on Aug. 13, 2007.
Declaration of John R. Brustad dated Dec. 10, 2009, submitted in U.S. Appl. No. 11/548,955, including Appendices A-D regarding product sales brochures and production drawings from 2001 and 2005.
The International Searching Authority, the International Search Report and Written Opinion of the International Searching Authority for International Application No. PCT/US08/63445, mailed Sep. 29, 2008.
The International Searching Authority, the International Search Report and Written Opinion of the International Searching Authority for International Application No. PCT/US08/063463 mailed Sep. 10, 2008.
The International Bureau of WIPO, International Preliminary Report on Patentability for International Application No. PCT/US2008/063463, dated Nov. 17, 2009, entitled "Surgical Retractor".
The International Bureau of WIPO, International Preliminary Report on Patentability for International Application No. PCT/US08/63445, issued Nov. 17, 2009, entitled "Surgical Retractor with Gel Pad".
International Searching Authority—US, International Search Report and Written Opinion of the International Searching Authority for International Application No. PCT/US04/25511, mailed Nov. 7, 2007.
International Bureau of WIPO, International Report on Patentability for International Application No. PCT/US04/25511, mailed Dec. 6, 2007.
European Patent Office, European Search Report for European Patent No. 11172709.5, dated Aug. 16, 2011.
European Patent Office, European Search Report for European Patent No. 11172706.1, dated Aug. 16, 2011.
US 5,344,646, Chen (withdrawn).
Co-Pending U.S. Appl. No. 10/381,220, filed Mar. 20, 2003; Title: Surgical Access Apparatus and Method.
Co-Pending U.S. Appl. No. 10/516,198, filed Nov. 30, 2004; Title: Wound Retractor.
Co-Pending U.S. Appl. No. 10/927,551, filed Aug. 25, 2004; Title: Surgical Access System.
Co-Pending U.S. Appl. No. 11/244,647, filed Oct. 5, 2005; Title: Surgical Access Apparatus and Method.
Co-Pending U.S. Appl. No. 11/245,709, filed Oct. 7, 2005; Title: Surgical Access System.
Co-Pending U.S. Appl. No. 11/330,661, filed Jan. 12, 2006; Title: Sealed Surgical Access Device.
Co-Pending U.S. Appl. No. 11/548,746, filed Oct. 12, 2006; Title: Method of Making a Hand Access Laparoscopic Device.
Co-Pending U.S. Appl. No. 11/548,758, filed Oct. 12, 2006; Title: Split Hoop Wound Retractor With Gel Pad.
Co-Pending U.S. Appl. No. 11/755,305, filed May 30, 2007; Title: Wound Retraction Apparatus and Method.
Co-Pending U.S. Appl. No. 11/548,767, filed Oct. 12, 2006; Title: Circular Surgical Retractor.
Horigane, et al., Technical Note: Development of a Duodoenal Cannula for Sheep, Journal of Animal Science, Apr. 1992, vol. 70, Issue 4, pp. 1216-1219.
Horigane, et al., Silicone Rumen Cannula with a Soft Cylindrical Part and a Hard Flange, Journal of Dairy Science, Nov. 1989, vol. 72, No. 11, pp. 3230-3232.
McSweeney, Cannullation of the Rumen in Cattle and Buffaloes, Australian Veterinary Journal, Aug. 1989, vol. 66, No. 8, pp. 266-268.
Yamazaki et al., Diurnal Changes in the Composition of Abomasal Digesta in Fasted and Fed Sheep, The Tohoku Journal of Argircultural Research, Mar. 1987, vol. 37, No. 3-4, pp. 49-58.
Co-Pending U.S. Appl. No. 11/548,781, filed Oct. 12, 2006; Title: Wound Retractor With Gel Cap.
Co-Pending U.S. Appl. No. 11/548,955, filed Oct. 12, 2006; Title: Hand Access Laparoscopic Device.
Co-Pending U.S. Appl. No. 11/564,409, filed Nov. 29, 2006; Title: Surgical Instrument Access Device.
Co-Pending U.S. Appl. No. 12/108,400, filed Apr. 23, 2008; Title: Wound Retraction Apparatus and Method.
Co-Pending U.S. Appl. No. 11/755,305, filed May 30, 2007 Title: Wound Retraction Apparatus and Method.
European Patent Office, International Search Report and the Written Opinion of the International Searching Authority for International Application No. PCT/2006/039883, mailed Jan. 31, 2007.
European Patent Office, International Search Report and the Written Opinion of the International Searching Authority for International Application No. PCT/2006/039905 mailed Jan. 17, 2007.
European Patent Office, International Search Report and the Written Opinion of the International Searching Authority for International Application No. PCT/2006/040073 mailed Jan. 26, 2007.
The International Bureau of WIPO, International Preliminary Report on Patentability dated Apr. 16, 2008 for PCT Application No. PCT/US2006/039799.
European Patent Office, International Search Report and the Written Opinion of the International Searching Authority for International Application No. PCT/US2006/040154, dated Jan. 23, 2007.
The International Bureau of WIPO, The International Preliminary Report on Patentability for International Application No. PCT/US06/40073 mailed Apr. 24, 2008.
Declaration of John R. Brustad Under 37 C.F. R. 1.132, dated Dec. 10, 2009.
"Applied GelPort™ Advanced Access Device" product sales brochure dated 2001.
"Cap Ring" production drawing dated Jan. 19, 2001.
"Gelport® Laparoscopic Hand Access System" product sales brochure dated 2005.
"Cap Ring Medium" production drawing dated Aug. 16, 2005.
European Patent Office, European Search Report for European Patent Application No. 10189325.3, dated Dec. 21, 2010, entitled "Split Hoop Wound Retractor".
European Patent Office, European Search Report for European Patent Application No. 10189327.9, dated Dec. 21, 2010, entitled "Split Hoop Wound Retractor".
European Patent Office, European Search Report for European Patent Application No. 10189328.7, dated Dec. 21, 2010, entitled "Split Hoop Wound Retractor".

SPLIT HOOP WOUND RETRACTOR

CROSS REFERENCE TO RELATED APPLICATIONS

This application is a continuation of U.S. patent application Ser. No. 11/548,765, filed Oct. 12, 2006, which claims the benefit of U.S. Provisional Application No. 60/726,826, filed on Oct. 14, 2005; U.S. Provisional Application No. 60/745,730, filed on Apr. 26, 2006; U.S. Provisional Application No. 60/803,346, filed on May 26, 2006; U.S. Provisional Application No. 60/803,965, filed on Jun. 5, 2006; and U.S. Provisional Application No. 60/828,089, filed Oct. 4, 2006, the entire disclosures of which are incorporated herein by reference.

BACKGROUND

This invention relates substantially to devices and other apparatuses facilitating sealed access with surgical instruments, such as a surgeon's hand, across a body wall and into a body cavity.

In several areas of surgery there exists a need to have mechanisms or devices that can seal a body cavity or space, and yet permit the introduction of surgical instruments such as guidewires, endoscopes, and even the hand of a surgeon. Typical of these areas of surgery is laparoscopic surgery that relies on surgical instruments inserted through the abdominal wall to reach an operative site within the abdominal cavity. In order to increase space around the operative site within the cavity, insufflation gases are typically introduced to inflate the cavity and elevate the abdominal wall. The pressurizing of the abdominal cavity is referred to as pneumoperitoneum. In this context, the need to seal the body cavity or space arises from the need to maintain the pneumoperitoneum even when instruments are present.

Trocars have been commonly used to provide instrument access in laparoscopic surgeries. These trocars have included elaborate seal structures having zero seals that prevent the escape of the gases in the absence of instruments, and instrument seals that prevent the escape of the gases in the presence of instruments. Unfortunately, the instrument seals have been able to accommodate only a narrow range of instrument diameters. Multiple seal pairs had to be provided where wider ranges were desired.

Some instruments, such as the hand of the surgeon, have been too large for trocar access. Under these circumstances, hand-assisted laparoscopic seals have been provided. Such devices have been large, cumbersome, and largely ineffective in providing the required sealing mechanism. Other access devices, such as Touhy-Borst seals, have been used, but only for very small diameter access such as that required by a guidewire.

Each of the prior devices suffers from drawbacks that make the device difficult or cumbersome to use. For example, a Touhy-Borst seal requires two hands to use and does not form a seal when a guidewire or other device is about to be introduced. Present trocar seals and hand-assisted seals require two valves, one forming an instrument seal in the presence of the instrument, and the other forming a zero seal in the absence of the instrument. For example, in hand-assisted devices, elaborate mechanisms have been required to seal around the surgeon's arm. When the arm is removed, a separate zero seal has been required to prevent the escape of blood or insufflation gases.

SUMMARY

The invention is directed to a gel cap that is adapted for being coupled to a wound retractor. The wound retractor has a substantially noncompliant outer ring that is adapted for juxtaposition with an outer surface of a biological body wall and for disposition relative to an incision in the body wall. The wound retractor also includes an inner ring that is adapted for juxtaposition with an inner surface of the biological body wall and for disposition relative to the incision in the body wall. The wound retractor further includes a sleeve that is adapted to traverse the incision in the body wall. The sleeve of the wound retractor couples the outer ring to the inner ring. The wound retractor is adapted to retract and seal the incision. The gelcap includes a cap ring and a gel pad. The cap ring includes a substantially cylindrical ring that has a first, proximal portion, a second, distal portion, and a plurality of lips at a distal end of the distal portion. Each of the lips curves radially inward from the wall of the distal portion of the cap ring and extends around a portion of the circumference of the cap ring. The gel pad, which is made of a gel material, is coupled to the cap ring and positioned at the proximal portion of the cap ring. The gel pad includes an access portion for providing a passage from external the biological body to a biological body cavity. The passage forms an instrument seal in the presence of an instrument inserted therethrough and a zero seal in the absence of an instrument inserted therethrough. The lips are configured to receive the outer ring of the wound retractor such that the outer ring is positioned between the lip and the gel pad. The gel pad is adapted to be placed in juxtaposition with the incision.

In one aspect, the proximal portion of the cap ring includes a plurality of apertures that are distributed about the circumference of the cap ring. The apertures extend through the wall of the proximal portion of the cap ring. In one aspect, the gel of the gel pad covers and fills the apertures. In another aspect, the gel in the apertures connects the gel at an outer portion of the cap ring to the gel at an inner portion of the cap ring. In another aspect, the gel of the gel cap extends into the distal portion of the cap ring. In one aspect, the distal portion of the cap ring is adapted to receive the outer ring of the wound retractor such that the outer ring of the wound retractor embeds into the gel pad at the distal portion of the cap ring and displaces the gel. Having the outer ring of the wound retractor embed into the gel pad forms a seal between the gel pad and the outer ring and sleeve of the wound retractor. In another aspect, the access portion of the gel pad includes a plurality of intersecting dead-end slits. In another aspect, the distal portion of the cap ring includes three lips that are substantially equally spaced about the circumference of the distal portion of the cap ring. In another aspect, each of the three lips extends about 60° around the circumference of the cap ring. In another aspect, the distal portion of the cap ring includes more than three lips. The more than three lips are substantially equally spaced about the circumference of the distal portion of the cap ring. In another aspect, the distal portion of the cap ring includes two lips. The two lips are substantially diametrically opposed about the circumference of the distal portion of the cap ring. Each of the two lips extends a sufficient distance around the circumference of the cap ring to facilitate adequate coupling of the gel cap to the outer ring of the wound retractor. In another aspect, the cap ring is made of a polymer. In one aspect, the polymer is polyethylene while in another aspect the polymer is polycarbonate. In another aspect, the gel pad covers and seals the entire opening in the cap ring. In another aspect, the gel pad is adapted to cover substantially the entire wound opening.

These and other features and advantages of the invention will become more apparent with a discussion of embodiments in reference to the associated drawings.

BRIEF DESCRIPTION OF THE DRAWINGS

FIG. 2b illustrates a perspective view of the wound retractor of FIG. 2a;

DETAILED DESCRIPTION

Figure 1:
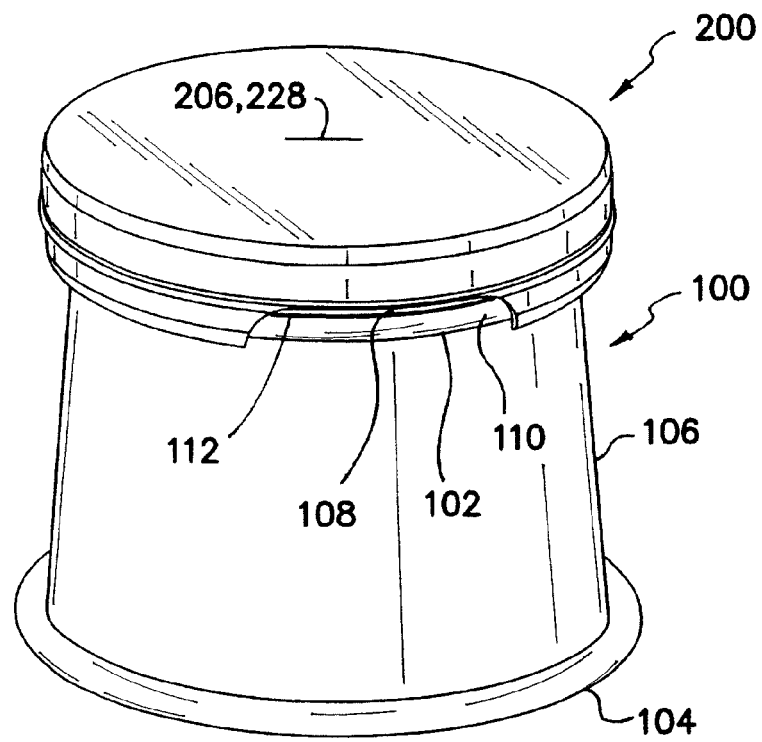
FIG. 1 is a top perspective view of a gel cap of the invention placed onto a wound retractor of the invention.
Figure 2A:
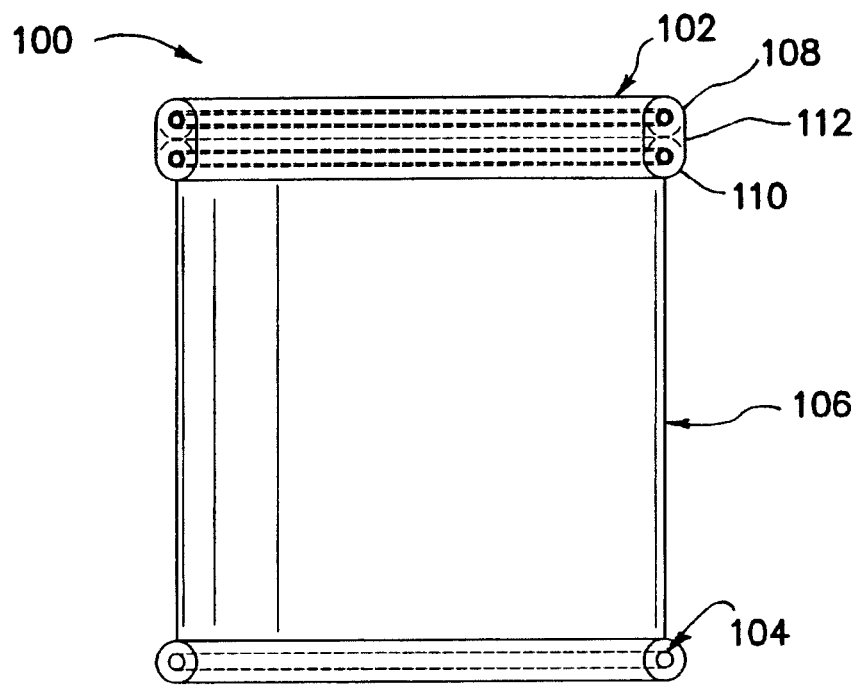
FIG. 2a illustrates an elevation view of an incrementally adjustable wound retractor in accordance with an embodiment of the invention.
Figure 2B:
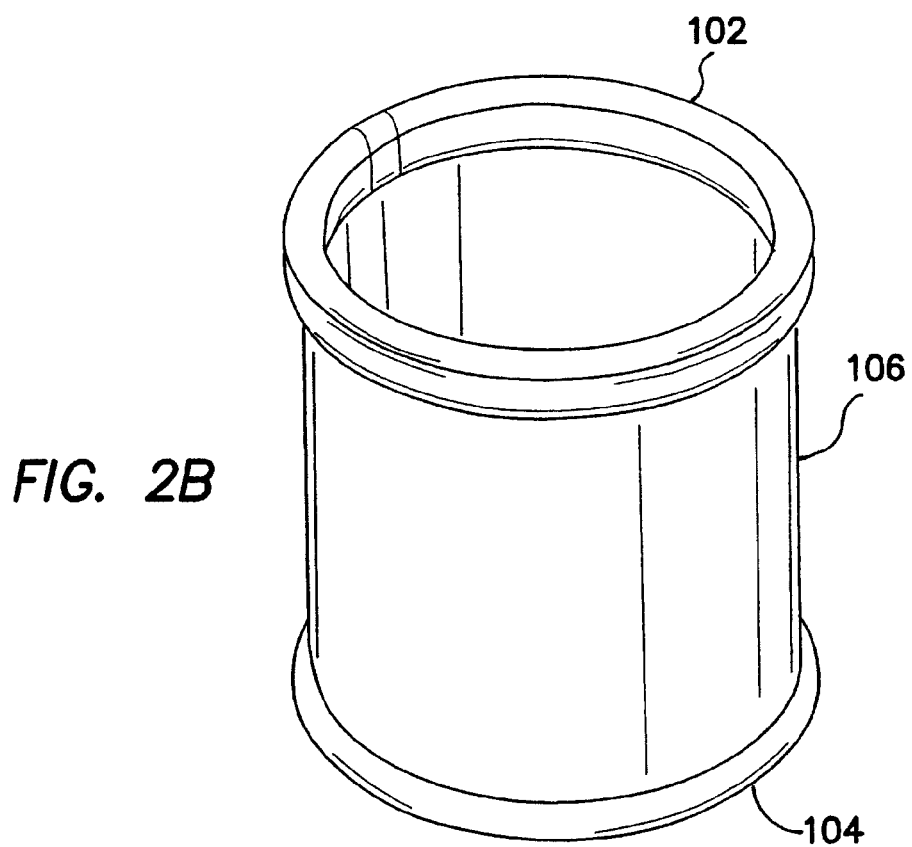

FIGS. 1, 2a and 2b illustrate a wound retractor 100 and gel cap 200 in accordance with an embodiment of the invention.

Figure 8:
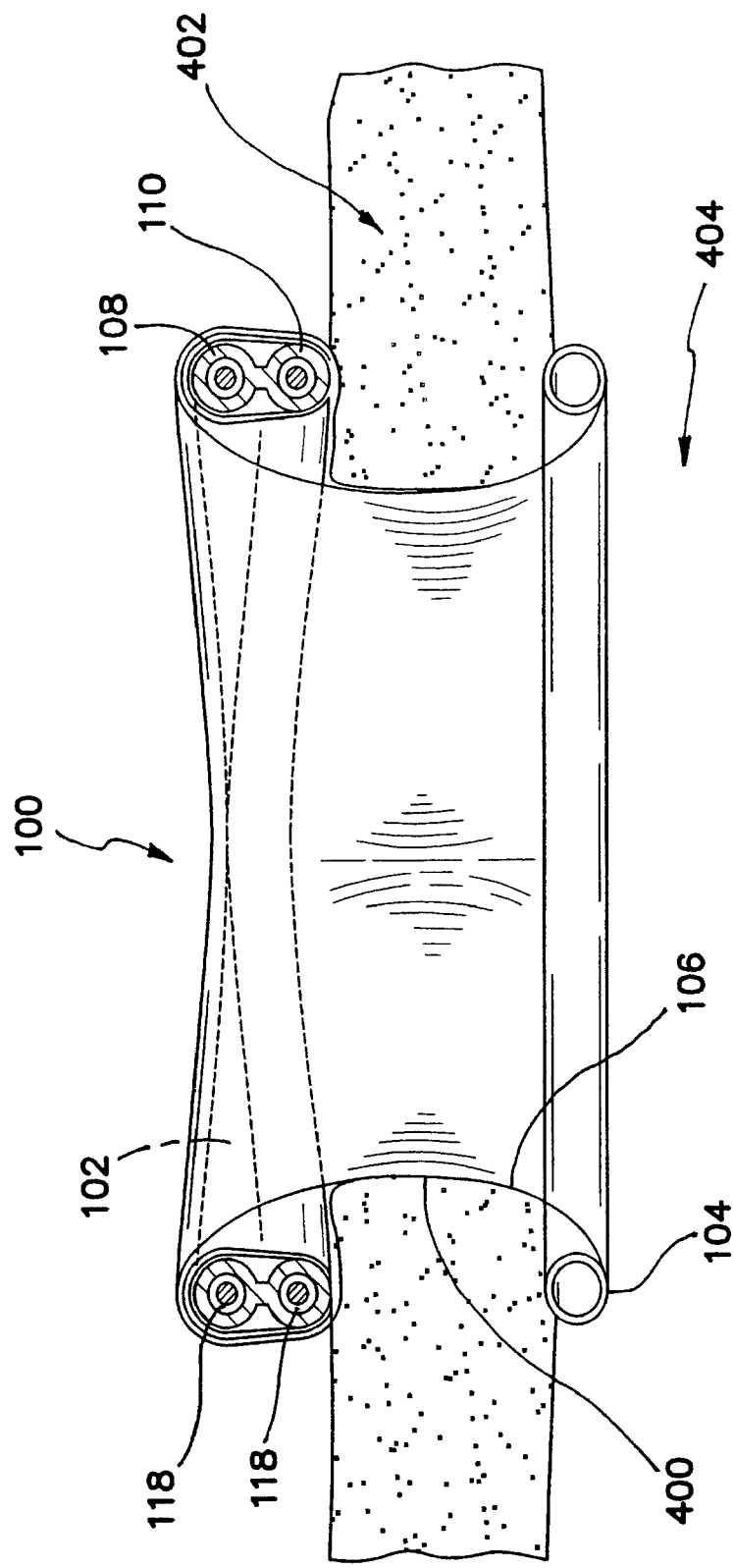
FIG. 8 illustrates the wound retractor of FIG. 1 deployed in an incision.
Figure 10:
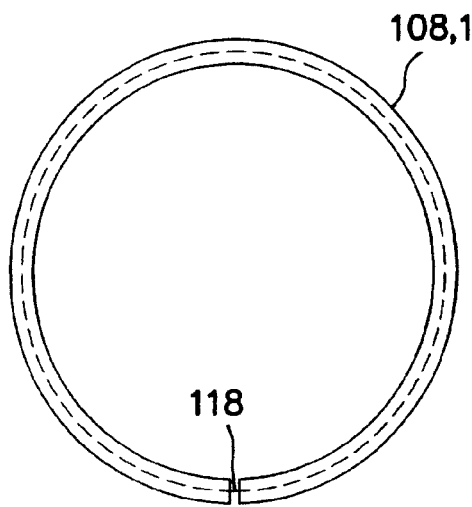
FIG. 10 depicts a plan view of one of the first and second circular tubes of the outer ring with a split hoop placed therein with the split hoop and circular tube in their neutral state.
Figure 11:
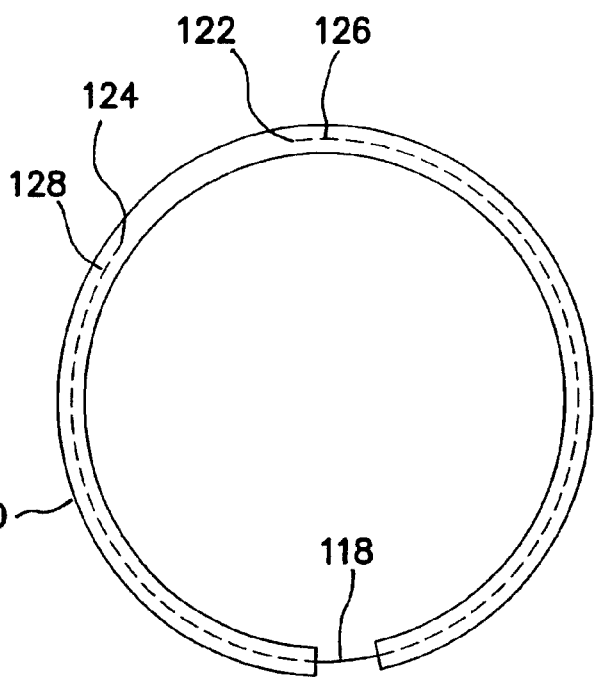
FIG. 11 depicts a plan view of one of the first and second circular tubes of the outer ring with a split hoop placed therein with the split hoop and circular tube in their expanded state.
Figure 12:
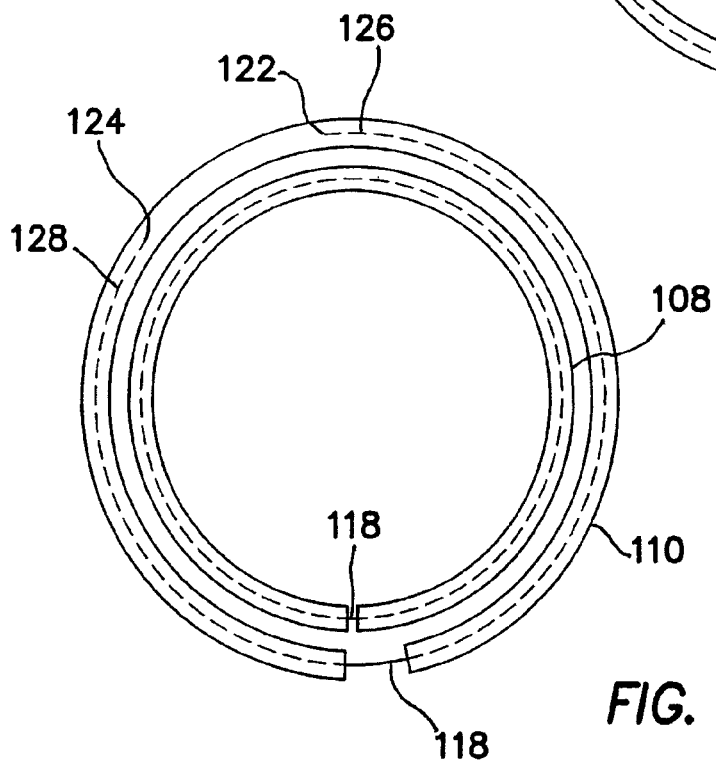
FIG. 12 depicts a plan view of the first circular tube and split hoop and the second circular tube and split hoop with the first circular tube and split hoop in their neutral state and the second circular tube and split hoop in their expanded state being rolled around the first circular tube and split hoop
Figure 13:
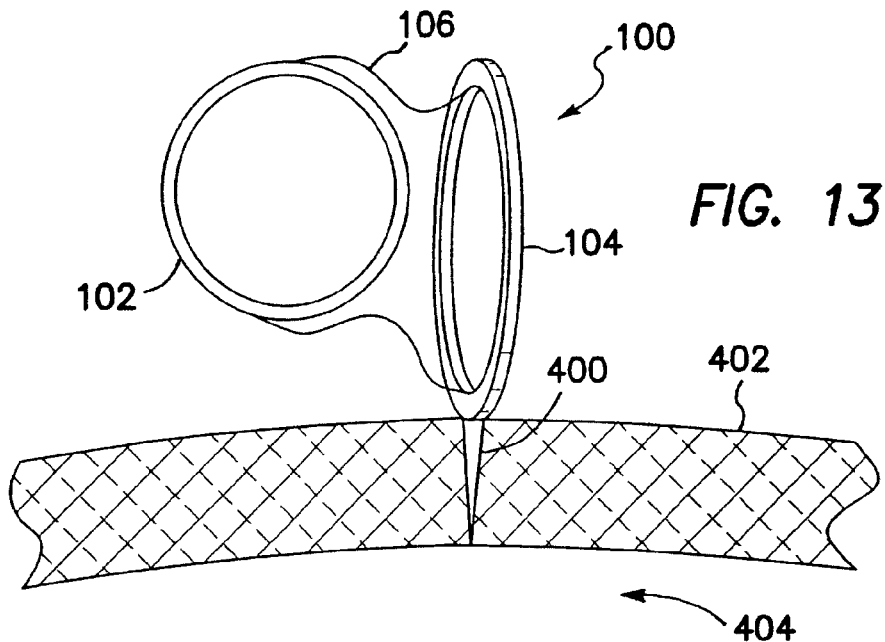
FIG. 13 is a side view of a wound retractor of the invention being inserted into a wound in a body wall with the inner ring being inserted into the wound.
Figure 14:
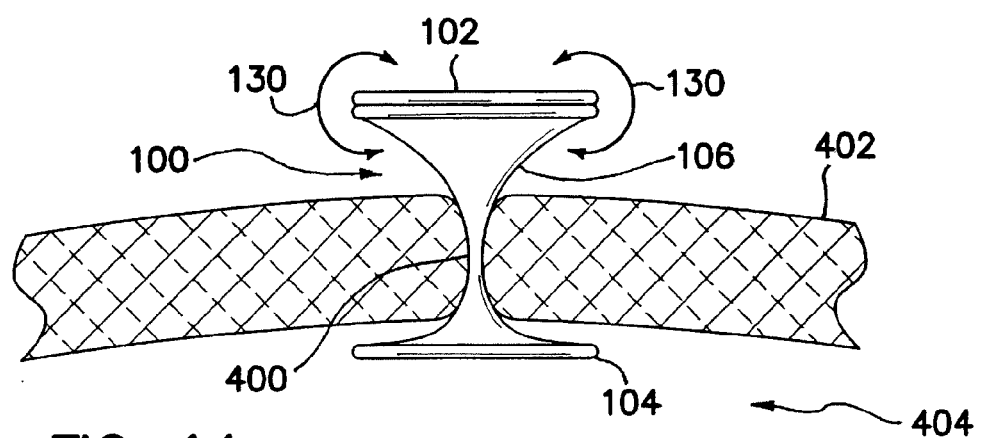
FIG. 14 is a side view of the wound retractor of the invention placed in the wound in the body wall and depicting a direction for rolling the outer ring to retract the wound.
Figure 15:
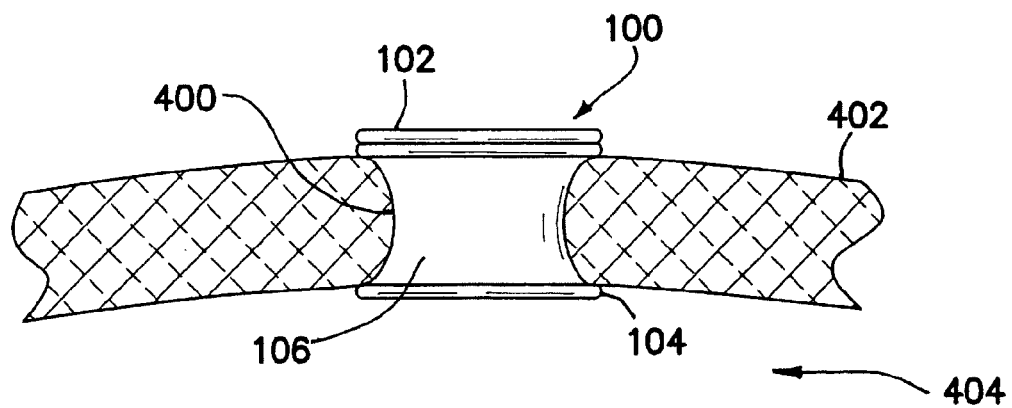
FIG. 15 is a side view of the wound retractor invention placed in the wound in the body wall with the wound retracted.
Figure 16:
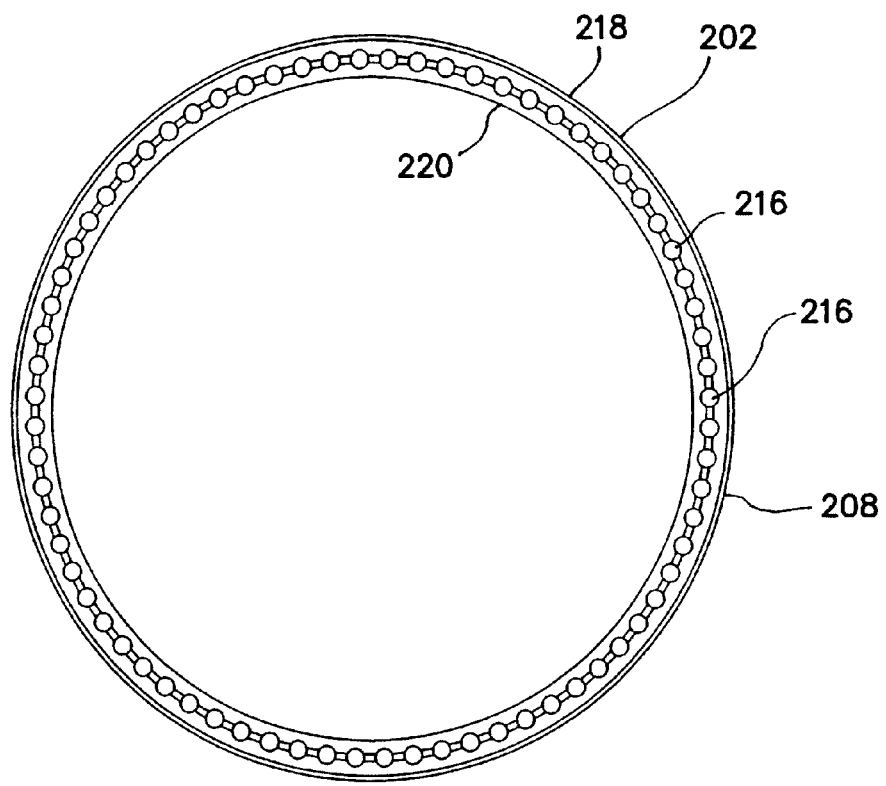
FIG. 16 is a top plan view of a cap ring portion of a gel cap of the invention configured for coupling the gel cap to the outer ring of the wound retractor.
Figure 19:
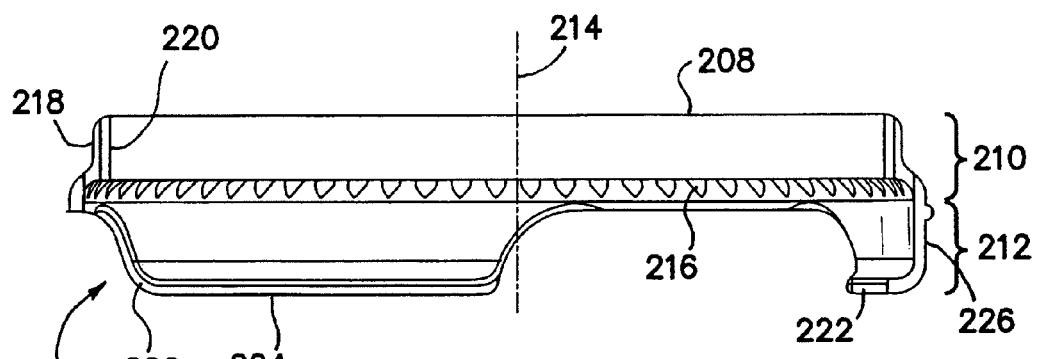
FIG. 19 is a side cross-sectional view of the cap ring of FIG. 16.
Figure 17:
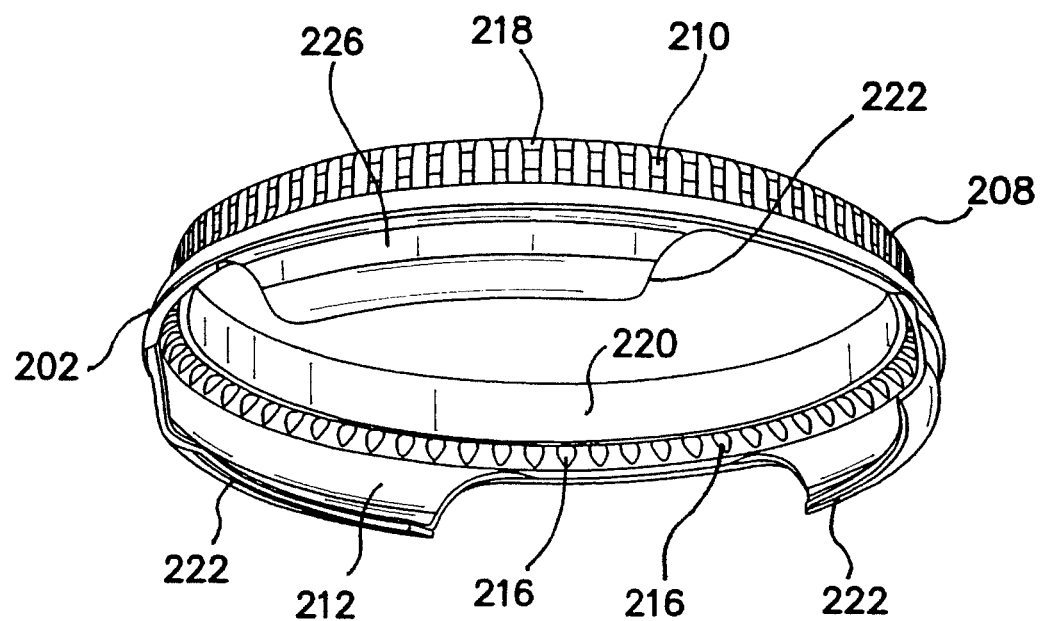
FIG. 17 is a bottom perspective view of the cap ring of FIG. 16 depicting lips for engaging the outer ring of the wound retractor.
Figure 18:
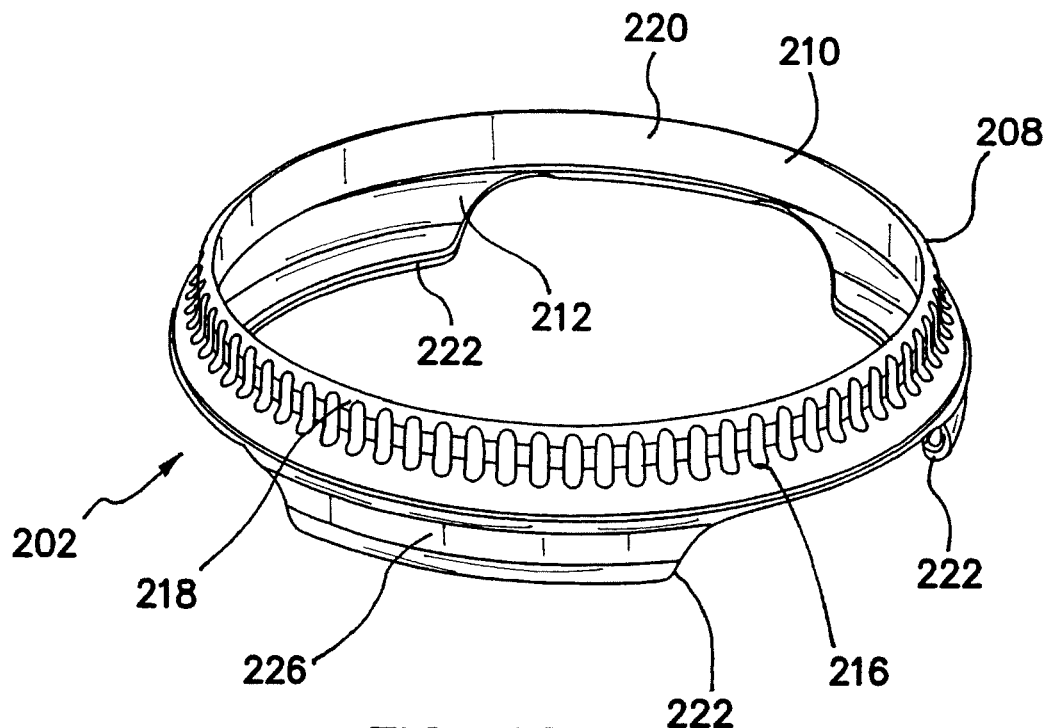
FIG. 18 is a top perspective view of the cap ring of FIG. 16.
Figure 20:
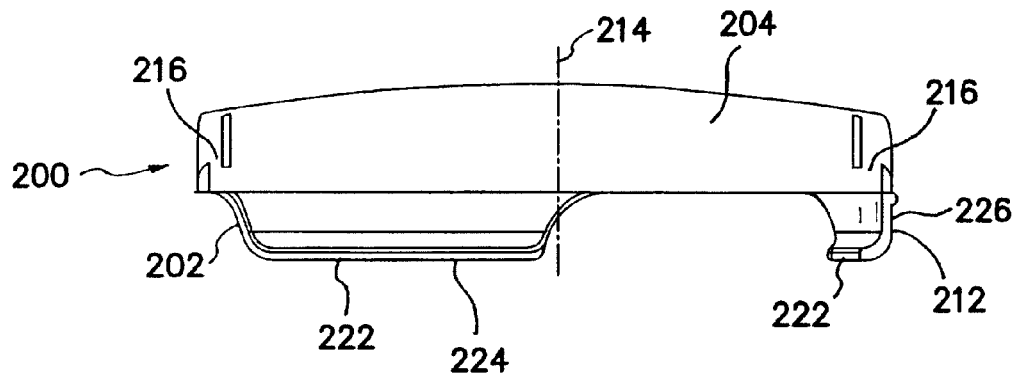
FIG. 20 is a side cross-sectional view of the gel cap incorporating the cap ring of FIG. 16.
Figure 21:
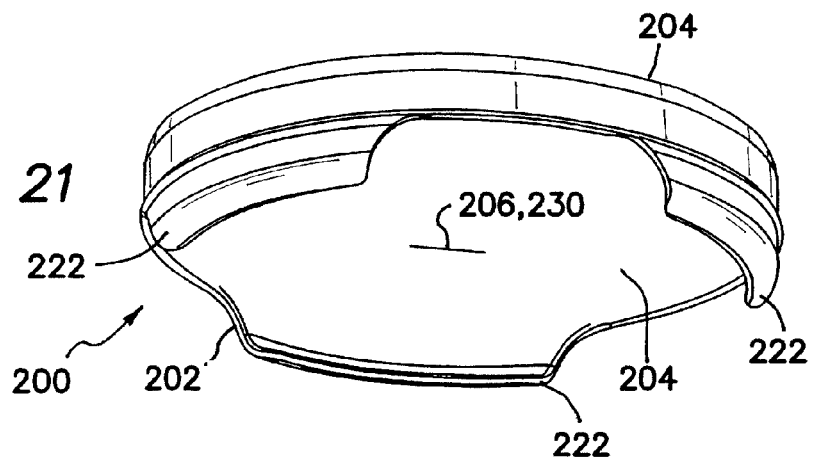
FIG. 21 is a bottom perspective view of the gel cap of FIG. 20.
Figure 22:
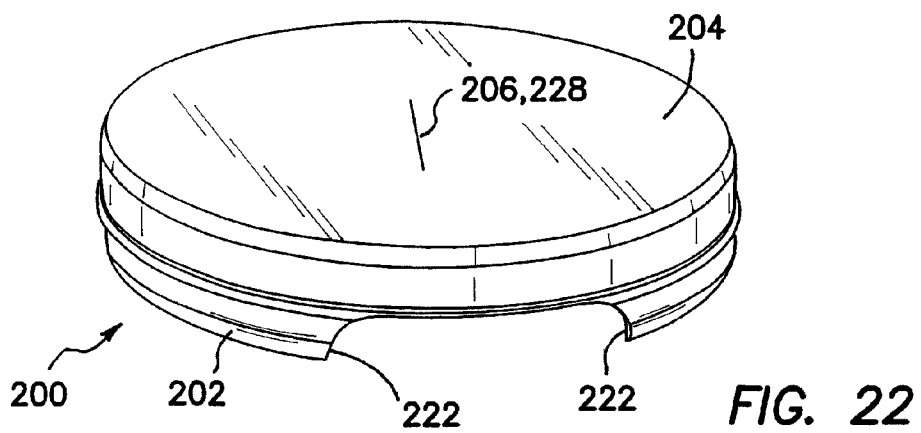
FIG. 22 is a top perspective view of the gel cap of FIG. 20.
Figure 23:
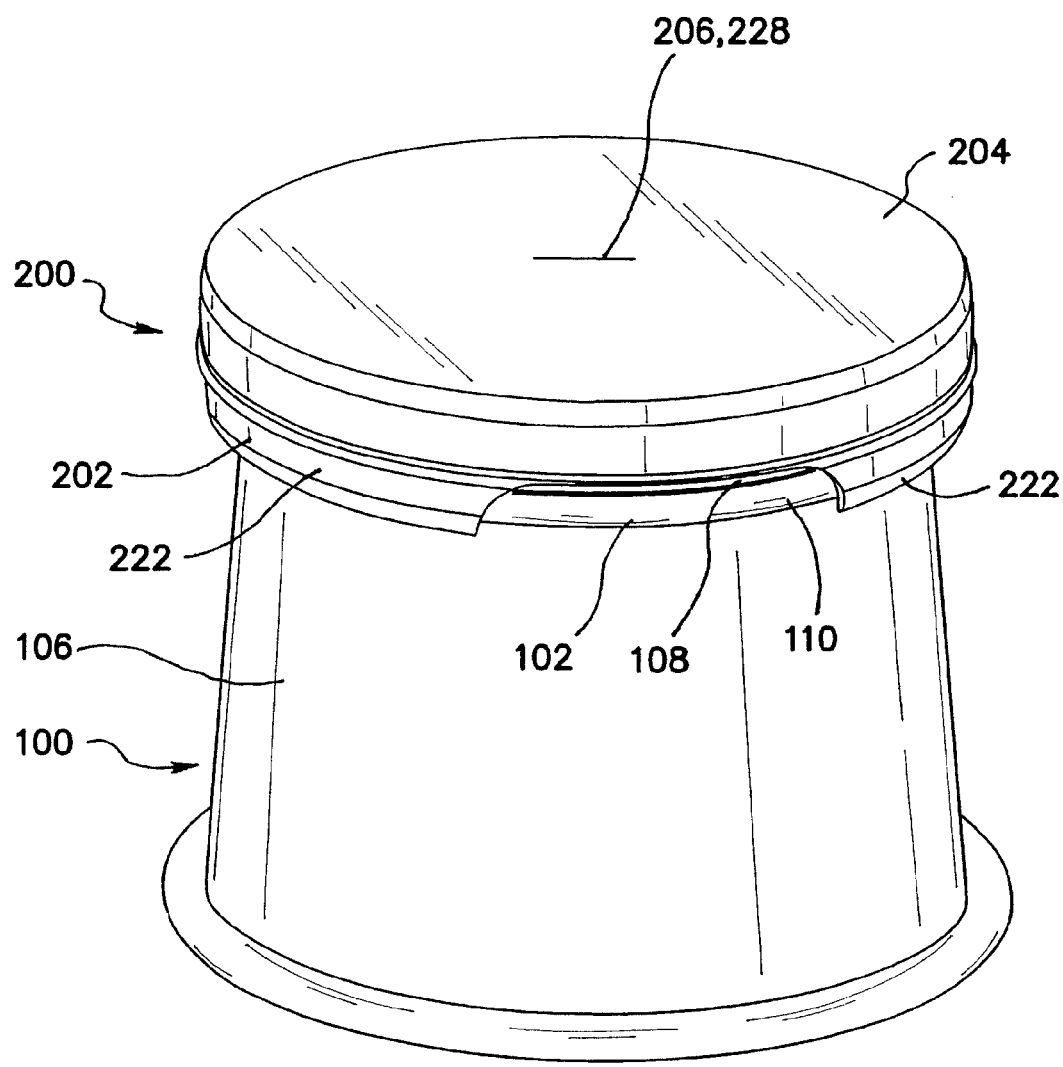
FIG. 23 is a top perspective view of the gel cap of FIG. 20 coupled to the outer ring of the wound retractor.
Figure 24:
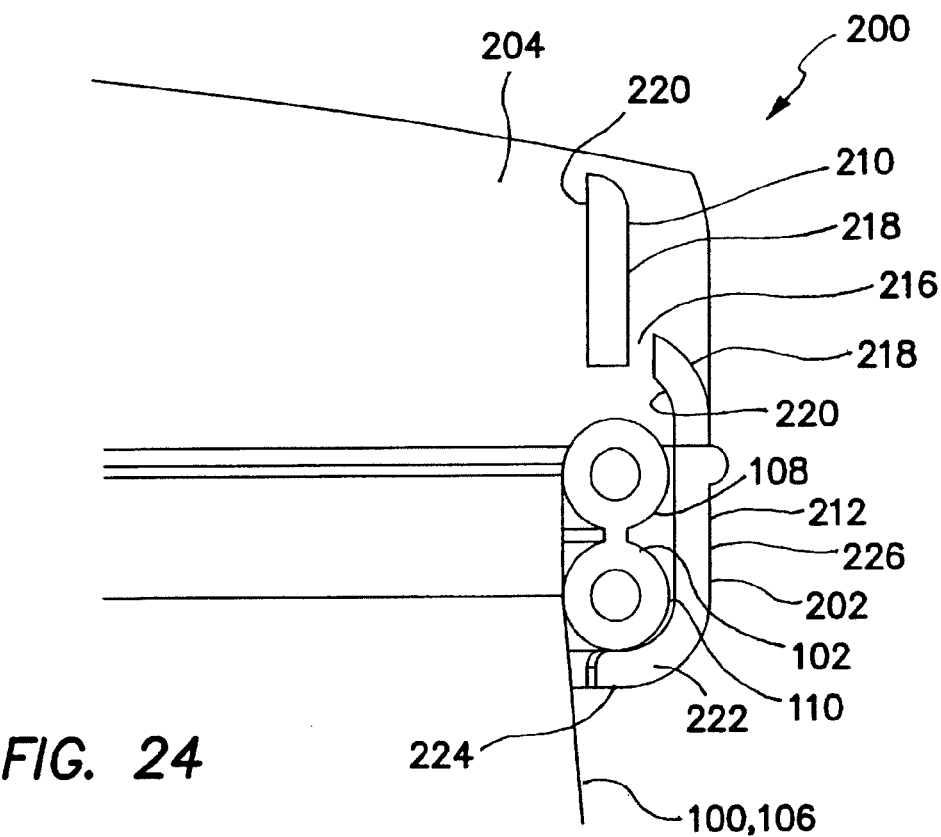
FIG. 24 is a partial section view of the gel cap of FIG. 20 coupled to the outer ring of the wound retractor.
Figure 25:
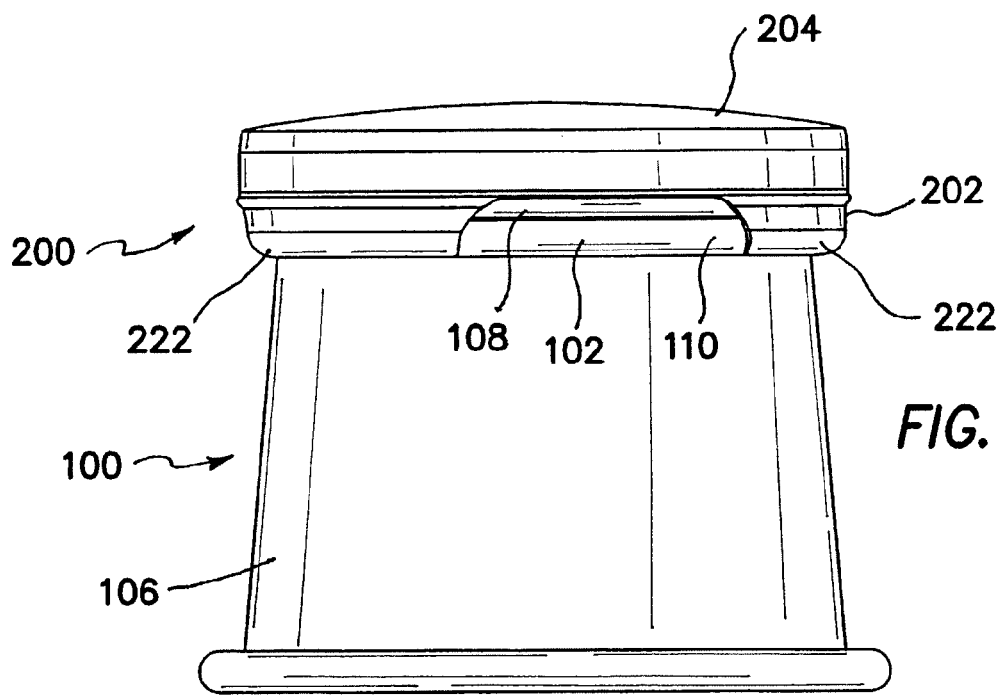
FIG. 25 is a side view of the gel cap of FIG. 20 coupled to the outer ring of the wound retractor.

The wound retractor 100 includes a double-tube outer ring 102, an inner ring 104, and a distensible sleeve 106 coupling the outer ring 102 to the inner ring 104. The sleeve 106 may be coupled to the outer ring 102 and the inner ring 104 by heat seal, adhesive, or other means that are well known in the art. The sleeve 106 may be made of a material that is flexible and impermeable to fluids and bacteria. The inner ring 104 may be made of materials having sufficient hardness to retain its shape after insertion of the inner ring into a body cavity 404 (FIG. 8). The materials of which the outer ring 102 is made must allow the outer ring 102 to be turned around its annular axis as further described below and illustrated in FIGS. 3a-3c. The shape of the outer ring 102 affects both its ability to grip and to provide stability during and after adjustment. The double-tube outer ring 102 includes a first circular tube 108 and a second circular tube 110 that are separated axially and may be coupled together by a small web 112. Each of the circular tubes 108 and 110 includes a lumen.

Figure 4:
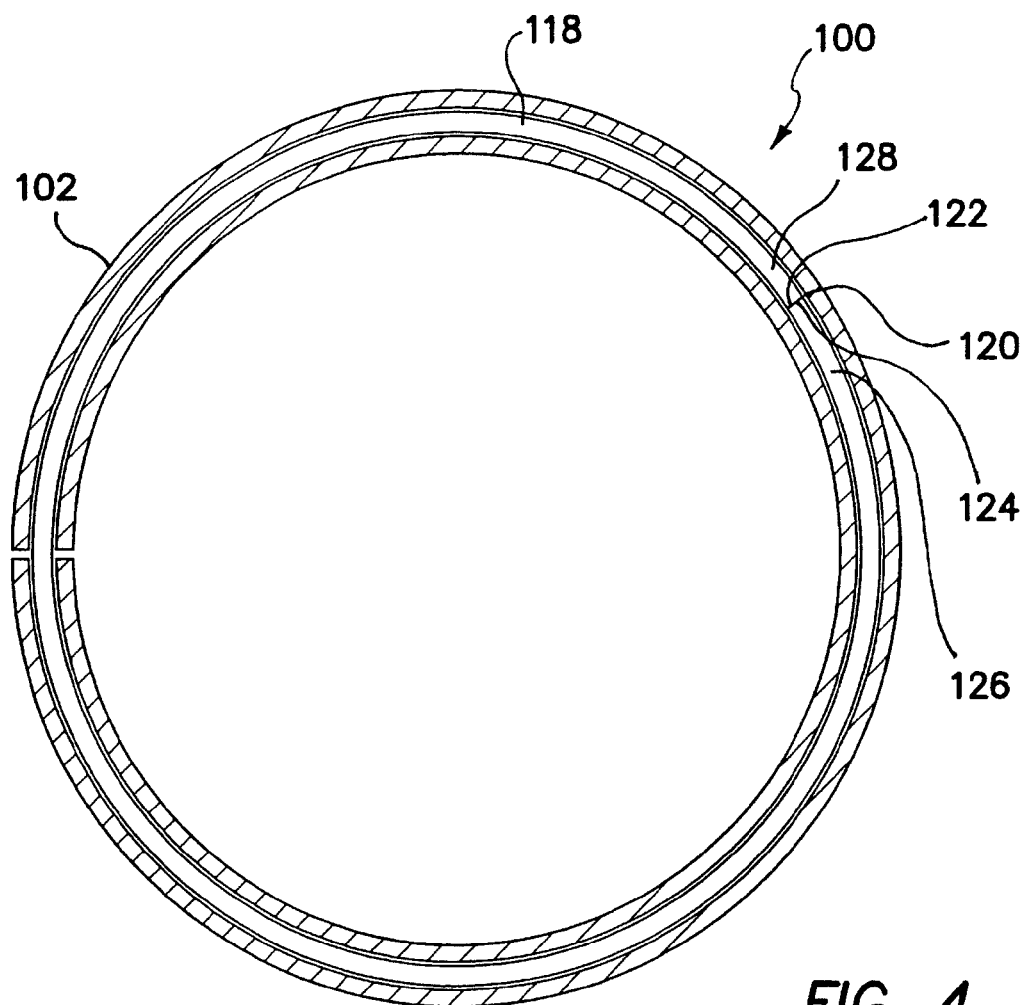
FIG. 4 depicts a plan view, in cross section, of the outer ring of the wound retractor having a split hoop in a lumen thereof.
Figure 5:
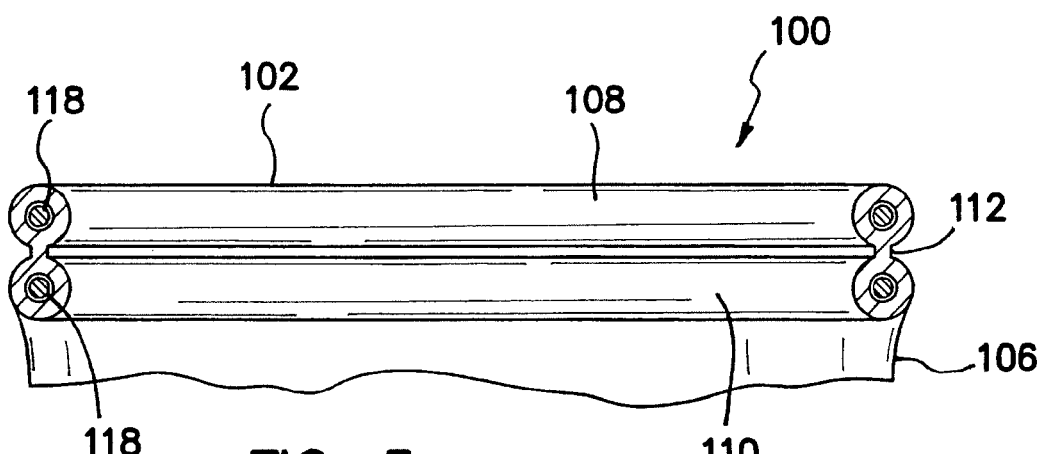
FIG. 5 depicts an elevation view of the outer ring of the wound retractor having a split hoop in the lumen of each of the first and second circular tubes of the outer ring.
Figure 6:
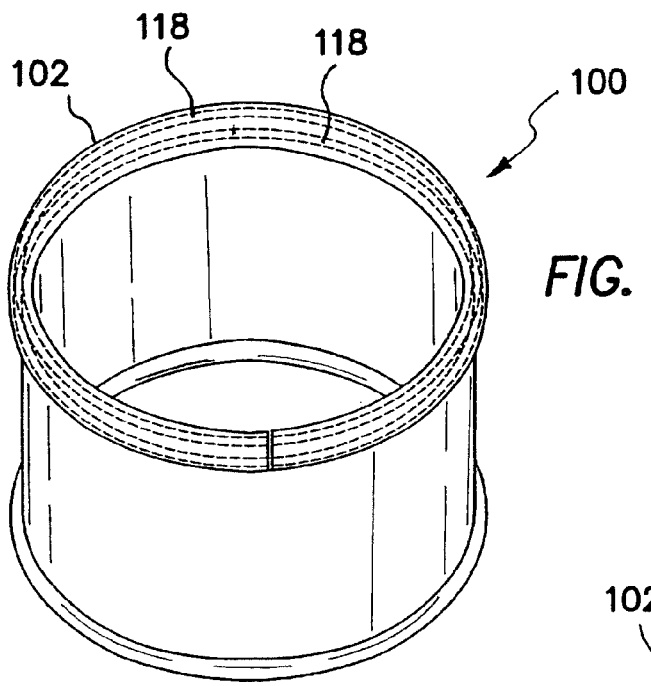
FIG. 6 depicts a perspective view of the wound retractor.

Referring to FIGS. 4-6, a wound retractor 100 may include the double-tube outer ring 102 having a substantially noncompliant, split hoop 118 positioned in the lumen of the first circular tube 108 and a substantially noncompliant, split hoop 118 positioned in the lumen of the second circular tube 110. Each of the split hoops 118 includes a hoop having a single split 120 about its circumference with the split creating a first end 122 of the split hoop and a second end 124 of the split hoop. In its neutral position, the first and second ends 122, 124 of the respective split hoops 118 substantially abut each other.

The substantially noncompliant hoops 118 may be made of metals, such as stainless steel, piano wire heat treated to a spring temper, or other metals that produce a substantially noncompliant hoop. The substantially noncompliant hoops 118 may also be formed of rigid polymeric materials through molding, machining, and other processes that are well known in the art. The substantially noncompliant hoops 118 may also be formed of other suitable rigid materials that are well known in the art.

Figure 7A:
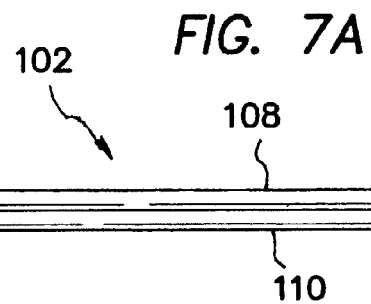
FIGS. 7a-7b illustrate different processes of forming the outer ring of the invention.
Figure 7B:
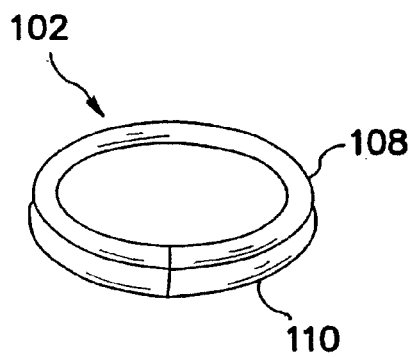
Figure 9:
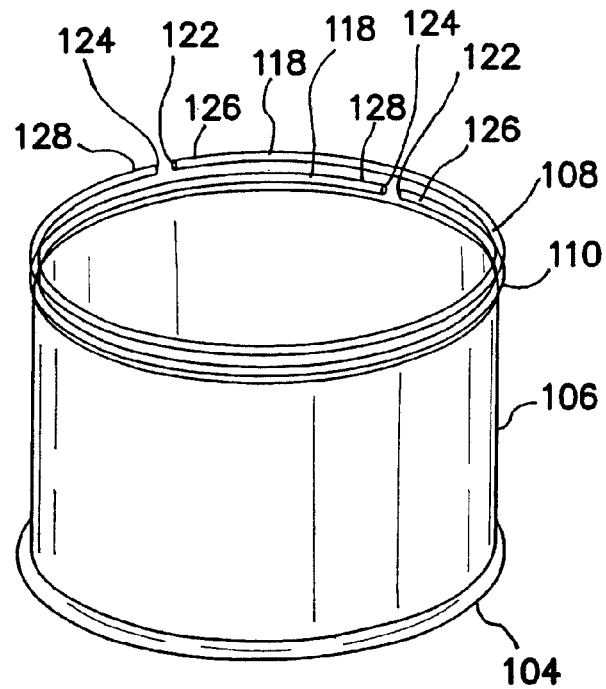
FIG. 9 depicts a perspective view of the wound retractor having the split hoops in the lumen of each of the first and second circular tubes of the outer ring.

As shown in FIGS. 7a-7b, the outer ring 102 may be formed by transforming an extruded elastomeric double-tube into a circular ring by placing the split hoops 118 (FIGS. 4-6) into the first and second circular tubes 108, 110. This is accomplished by inserting one of the first and second ends 122, 124 of one of the hoops 118 into the lumen of the first circular tube 108 and one of the first and second ends of the other hoop 118 into the lumen of the second circular tube 110. The split hoops 118 are continually fed into the lumens until substantially each of the entire hoops 118 is within the respective circular tubes 108, 110. The extruded elastomeric tube 102 takes on the circular shape of the split hoops 118 placed in the lumens of the first and second circular tubes 108, 110.

It is appreciated that the outer ring 102 can be designed in various configurations and sizes to achieve various retraction rates and/or to conform to different body surfaces. The lumens of the first and second circular tubes 108, 110 may have cross-sections of different geometries, such as circular, oval, triangular, rectangular, any geometric shape with multiple sides, etc. The split hoops 118 may also have cross-sections of different geometries, such as circular, rectangular, oval, triangular, any geometric shape with multiple sides, etc. Advantages of the above embodiments of the invention include improved retraction adjustability and stability.

With continued reference to FIGS. 4-6 and with reference to FIGS. 7a, 7b and 8-12, with each of the first and second circular tubes 108, 110 including a split hoop 118, it is not necessary to provide means for a first end portion 126 and a second end portion 128 of the split hoop to overlap each other when rolling the sleeve 106 around the outer ring 102. Since the split hoop 118 in the each of the first and second circular tubes 108, 110 has substantially abutting first and second ends 122, 124 and no means are provided for the first and second end portions 126, 128 of the split hoops to overlap each other, each of the split hoops 118 functions as an axle about which the outer ring 102 may turn for half a rotation, or 180°. More particularly, the first circular tube 108 may be rolled outside the second circular tube 110 with the circumference of the split hoop 118 in the first circular tube expanding to clear the split hoop 118 in the second circular tube. Then the second circular tube 110 may be rolled outside the first circular tube 108 with the circumference of the split hoop 118 in the second circular tube expanding to clear the split hoop 118 in the first circular tube (see FIG. 12). These steps may be repeated until the wound 400 is retracted to the desired degree.

FIGS. 3a-3c and FIG. 8 illustrate the retraction and adjustment of the outer ring 102 to fit an incision. In accordance with the invention, the wound retractor 100 is axially adjustable in increments. In particular, the upper end of the sleeve 106 can be wrapped around the outer ring 102 so as to tightly seal the sides or edges of the incision 400. The unique shape of the outer ring 102 provides for an easy snap action when rolled about itself. The outer ring 102 also provides for incremental shortening of the sleeve 106 and for stability after installation.

FIGS. 8 and 13-15 illustrate a process of installing the wound retractor 100 in a wound opening 400. An incision 400 in the shape of a slit is first made in a body wall of a patient, such as the abdominal wall 402. The inner ring 104 is compressed and the inner ring and sleeve 106 are then manually inserted into the body cavity 404 through the incision 400 with the outer ring 102 remaining external the body cavity 404. Once the inner ring 104 is within the body cavity 404, it expands around the inner surface of the incision 400 so as to be generally parallel to the outer surface of the abdominal wall 402. The sleeve 106 provides a working channel from outside the body cavity 404 to inside the body cavity.

Figure 3A:
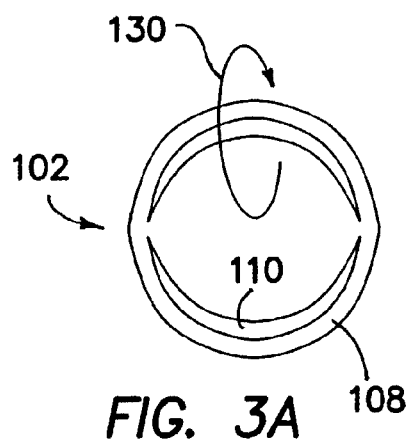
FIGS. 3a-3c illustrate the retraction of the outer ring of the wound retractor of FIG. 1 to retract an incision.
Figure 3B:
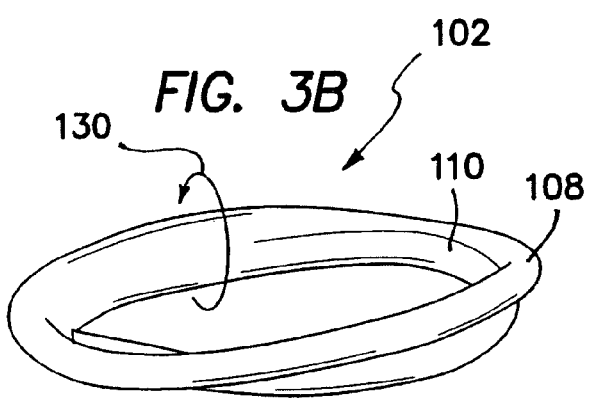
Figure 3C:
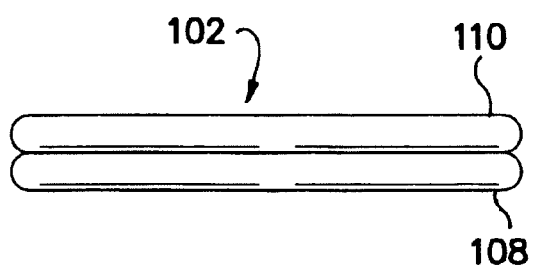

The outer ring 102 initially rests above the abdominal wall 402 around the wound opening 400. Since the upper end of the sleeve 106 is coupled to the outer ring 102, the sleeve 106 can be drawn upwards and radially outward or inward, thereby drawing the inner ring 104 tightly against the inner surface of the abdominal wall 402. Moreover, the intermediate portion of the sleeve 106 is drawn tightly against the sides and edges of the wound opening 400, thereby retracting the adjacent tissue and producing a tightly sealed opening to the body cavity 404. The sleeve 106 contacts the entire surface of the wound 400 and protectively covers and seals it from contamination and infection. Depending on the size and depth of the incision 400, the user can roll up the sleeve 106 by gripping the double-tube outer ring 102 and turning it in a direction 130, as also illustrated in FIGS. 3a-3c, until the sleeve 106 abuts the outer edge of the wound opening 400. The inner ring 104 is adapted for juxtaposition with the inner surface of the abdominal wall 402 and the outer ring 102 is adapted for juxtaposition with the outer surface of the abdominal wall. Both the inner ring 104 and the outer ring 102 are adapted for disposition relative to the incision 400 in the abdominal wall 402. The sleeve 106 is adapted to traverse the incision 400 in the abdominal wall 402.

An advantage of the wound retractor 100 of the present invention is it provides for an easier, faster and higher retraction rate than that known in the prior art, thereby resulting in less traumatic effects to the patient. Another advantage of the wound retractor 100 of the present invention is it provides tactile gripping and incremental rolling of the sleeve 106 about the outer ring 102. In comparison to retractors of the prior art, the substantially noncompliant hoops 118 in the lumens of the outer ring 102 provide greater strength, which in turn provides better retraction. The substantially noncompliant hoops 118 control the shape of the wound opening 400, rather than the wound opening controlling the shape of the wound retractor 100. In this manner, the wound retractor 100 of the present invention provides better isolation, protection, and sealing of the wound 400.

After surgery, the wound retractor 100 may be retrieved by grabbing the inner is ring 104 and the sleeve 106 and pulling them through the wound opening 400. The use of the sleeve 106 and the ease of retracting the outer ring 102 provide higher compression between the inner and outer rings. As a result, the wound retractor 100 of the invention provides incremental adjustability to fit a wide range of incision sizes and isolates and protects the wound from bacterial infection as diseased body parts and contaminated instruments are passed through the wound.

Referring to FIGS. 16-25, the gel cap 200 includes a cap ring 202 that couples to the outer ring 102 of the wound retractor 100 and a gel pad 204 coupled to the cap ring. The gel pad 204 is made of a gel material and includes an access portion 206 or passage through the gel for providing a passage from external the body to the body cavity 404. In one aspect, the access portion 206 may include a plurality of intersecting dead-end slits 228, 230. The access portion 206 forms an instrument seal in the presence of an instrument, such as the arm of a surgeon, inserted therethrough and a zero seal in the absence of an instrument inserted therethrough.

To combine the gel pad 204 with the cap ring 202, the cap ring may be placed into a mold that includes the shape of the desired gel pad and the uncured gel is added to the mold. In one aspect, the cap ring 202 includes a substantially cylindrical ring 208 having a first, proximal portion 210, a second, distal portion 212 and a longitudinal axis 214 extending through the proximal and distal portions. The gel pad 204 is positioned at the proximal portion 210 of the cap ring 202. The proximal portion 210 of the cap ring 202 may include a plurality of apertures 216 distributed about the circumference of the cap ring. The apertures 216 may extend through the wall of the proximal portion 210 of the cap ring 202. Sufficient gel may be added to the mold to cover and fill the apertures 216. When adding uncured gel into the mold, the gel flows through the apertures 216 and remains in the apertures. Also, for reasons that will be described below, sufficient gel may be added to the mold to extend into the distal portion 212 of the cap ring 202. When the gel pad 204 is cured, the gel in the apertures 216 connects the gel at the outer portion 218 of the cap ring 202 to the gel at the inner portion 220 of the cap ring, thus forming a mechanical lock between the gel and the cap ring. Alternatively, as will be described below, a separately formed gel slug 204 may be coupled to the inner surface of the proximal portion 210 of the cap ring 202.

The distal portion 212 of the cap ring 202 is substantially cylindrical and is configured to receive the outer ring 102 of the wound retractor 100. In one aspect, the distal portion 212 of the cap ring 202 includes a plurality of lips 222 at the distal end 224 thereof. The lips 222 curve radially inwardly from the wall 226 of the distal portion 212 of the cap ring 202 and extend around a portion of the circumference of the cap ring. In one aspect, there are three lips 222 that are substantially equally spaced about the circumference of the distal portion 212 of the cap ring 202. Each of the three lips 222 may extend about 60° around of the circumference of the cap ring 202, however, the lips may extend longer or shorter distances around the circumference of the cap ring. Also, there may be more than three lips 222 with each lip extending a shorter distance around the circumference of the cap ring 202 and the more than three lips being substantially equally spaced about the circumference of the distal portion of the cap ring. In another aspect, there may be two lips 222 that are substantially diametrically opposed about the circumference of the distal portion of the cap ring with each of the lips extending a sufficient distance around the circumference of the cap ring 202 to facilitate adequate coupling of the gel cap 200 to the outer ring 102 of the wound retractor 100. The lips 222 are configured to receive the distal-most circular tube 108, 110 of the outer ring 102 of the wound retractor 100 such that the outer ring is positioned between the lips 222 and the gel pad 204. More particularly, when the outer ring 102 of the wound retractor 100 is received by the distal portion 212 of the cap ring 202, the outer ring of the wound retractor embeds into the gel pad 204 at the distal portion 212 of the cap ring 202 and displaces the gel, thereby forming a seal between the gel pad and the outer ring and sleeve 106 of the wound retractor. This places the gel pad 204 in juxtaposition with the incision 400.

In use, the wound retractor 100 is first used to retract the incision in the body wall of a patient, as described above. The gel cap 200 is brought to the outer ring 102 of the wound retractor 100 at an angle, with one of the lip portions 222 of the cap ring 202 toward the patient. The lip portion 222 of the cap ring that is toward the patient is slid under the distal-most circular tube 108, 110 of the outer ring 102, between the outer ring and the patient, and then the remainder of the gel cap 200 is swung onto the outer ring with the remaining lip portions snapping into place under the distal-most circular tube. In an alternative aspect, the gel cap 200 may be brought to the outer ring 102 substantially parallel to the outer ring and the lip portions 222 snapped into place under the distal-most circular tube 108, 110 of the outer ring 102 at the same time.

The gel cap 200 with the plurality of lips 222 on the cap ring 202 is best suited for use with wound retractors 100 having an outer ring 102 that is substantially rigid and noncompliant. If the outer ring 102 of the wound retractor 100 were not rigid, the outer ring would tend to pull out of the gel cap 200, thereby compromising the seal between the gel pad 204 and the wound retractor and potentially resulting in deflation of the insufflated body cavity.

The cap ring 202 in one aspect includes a polymer, e.g., polyethylene (PE). In one aspect, the polyethylene is a low density polyethylene (LDPE) or high density polyethylene (HDPE), or ultra high molecular weight polyethylene (UHMWPE). In one aspect, the cap ring 202 may be made of a polymer, such as polycarbonate and may be fabricated by methods including injection molding.

The gel pad 204 may be coupled to, attached to, formed or integrated with the cap ring 202 so that a gas-tight conduit is formed between the cap ring and the sleeve 106. The gel pad 204 covers and seals the entire opening in the cap ring 202. Additionally, the gel pad 204 is adapted to cover substantially the entire wound 400 opening. As stated above, in one aspect the gel pad includes a plurality of intersecting dead-end slits 228, 230 that form an access portion or passage through the gel pad 204. Unlike foam rubber or other similar types of elastic materials, the gel pad 204 provides a gas tight seal around a variety of shapes and sizes of hands or instruments inserted therethrough.

In one aspect, the gel material from which the gel pad 204 is made is an elastomeric gel. Some such gels have been described in U.S. patent application Ser. No. 10/381,220, filed Mar. 20, 2003, the disclosure of which is hereby incorporated by reference as if set forth in full herein. The gel can be prepared by mixing a triblock copolymer with a solvent for the midblocks. The endblocks are typically thermoplastic materials such as styrene and the midblocks are thermoset elastomers such as isoprene or butadiene, e.g., Styrene-Ethylene-Butylene-Styrene (SEBS). In one aspect, the solvent used is mineral oil. Upon heating this mixture or slurry, the midblocks are dissolved into the mineral oil and a network of the insoluble endblocks forms. The resulting network has enhanced elastomeric properties over the parent copolymer. In one aspect, the triblock copolymer used is KRATON G1651, which has a styrene to rubber ratio of 33/67. Once formed, the gel is substantially permanent and, by the nature of the endblocks, processable as thermoplastic elastomers henceforward. The mixture or slurry has a minimum temperature at which it becomes a gel, i.e., the minimum gelling temperature (MGT). This temperature, in one aspect, corresponds to the glass transition temperature of the thermoplastic endblock plus a few degrees. For example, the MGT for the mixture of KRATON G1651 and mineral oil is about 120° C. When the slurry reaches the MGT and the transformation to a gel state takes place, the gel becomes more transparent, thereby providing means for visually confirming when the transformation of the slurry to the gel state is substantially complete and that the gel may be cooled. In addition to triblocks, there are also diblock versions of the materials that may be used where Styrene is present at only one end of the formula, for example, Styrene-Ethylene/Butylene (SEB).

For a given mass of slurry to form into a complete gel, the entire mass of the slurry is heated to the MGT and remains heated at the MGT for sufficient time for the end blocks to form a matrix of interconnections. The slurry will continue to form into gel at temperatures above the MGT until the slurry/gel reaches temperatures at which the components within the slurry/gel begin to decompose or oxidize. For example, when the slurry/gel is heated at temperatures above 250° C., the mineral oil in the slurry/gel will begin to be volatile and oxidize. Oxidizing may cause the gel to turn brown and become oily.

The speed at which a given volume of slurry forms a gel is dependant on the speed with which the entire mass of slurry reaches the MGT. Also, with the application of temperatures higher than the MGT, this speed is further enhanced as the end block networks distribute and form more rapidly.

The various base formulas may also be alloyed with one another to achieve a variety of intermediate properties. For example, KRATON G1701X is a seventy percent (70%) SEB thirty percent (30%) SEBS mixture with an overall Styrene to rubber ratio of 28/72. It can be appreciated that an almost infinite number of combinations, alloys, and Styrene to rubber ratios can be formulated, each capable of providing advantages to a particular embodiment of the invention. These advantages will typically include low durometer, high elongation, and good tear strength.

It is contemplated that the gel material may also include silicone, soft urethanes and even harder plastics that might provide the desired sealing qualities with the addition of a foaming agent. The silicone material may be of the types currently used for electronic encapsulation. The harder plastics may include PVC, Isoprene, KRATON neat, and other KRATON/oil mixtures. In the KRATON/oil mixture, oils such as vegetable oils, petroleum oils and silicone oils may be substituted for the mineral oil.

Any of the gel materials contemplated could be modified to achieve different properties such as enhanced lubricity, appearance, and wound protection. Additives may be incorporated directly into the gel or applied as a surface treatment. Other compounds may be added to the gel to modify its physical properties or to assist in subsequent modification of the surface by providing bonding sites or a surface charge. Additionally, oil based colorants may be added to the slurry to create gels of different colors.

In one aspect, the mixture/slurry used with the various embodiments of the cap rings that are described herein are composed of about ninety percent (90%) by weight of mineral oil and about ten percent (10%) by weight of KRATON G1651. From a thermodynamic standpoint, this mixture behaves similar to mineral oil. Mineral oil has a considerable heat capacity and, therefore, at about 130° C. it can take three (3) or four (4) hours to heat a pound of the slurry sufficiently to form a homogeneous gel. Once formed, the gel can be cooled as quickly as practical with no apparent deleterious effects on the gel. This cooling, in one aspect, is accomplished with cold-water immersion. In another aspect, the gel may be air-cooled. Those familiar with the art will recognize that other cooling techniques that are well known in the art may be employed and are contemplated as within the scope of the present invention.

Many of the properties of the KRATON/oil mixture will vary with adjustments in the weight ratio of the components. In general, the greater the percentage of mineral oil the less firm the mixture; the greater the percentage of KRATON, the more firm the mixture. If the resultant gel is too soft it can lead to excessive tenting or doming of the gel cap during surgery when a patient's abdominal cavity is insufflated. Excessive tenting or doming may cause the slits 228, 230 to open, providing a leak path. Additionally, if the gel is too soft it might not provide an adequate seal. However, the gel should be sufficiently soft to be comfortable for the surgeon while simultaneously providing good sealing both in the presence of an instrument and in the absence of an instrument.

If the slurry is permitted to sit for a prolonged period of time, the copolymer, such as KRATON, and the solvent, such as mineral oil, may separate. The slurry may be mixed, such as with high shear blades, to make the slurry more homogeneous. However, mixing the slurry may introduce or add air to the slurry. To remove air from the slurry, the slurry may be degassed. In one aspect, the slurry may be degassed in a vacuum, such as within a vacuum chamber. In one aspect, the applied vacuum may be 0.79 meters (29.9 inches) of mercury, or about one (1.0) atmosphere. The slurry may be stirred while the slurry is under vacuum to facilitate removal of the air. During degassing within a vacuum, the slurry typically expands, then bubbles, and then reduces in volume. The vacuum may be discontinued when the bubbling substantially ceases. Degassing the slurry in a vacuum chamber reduces the volume of the slurry by about ten percent (10%). Degassing the slurry helps reduce the potential of the finished gel to oxidize.

Degassing the slurry tends to make the resultant gel firmer. A degassed slurry composed of about 91.6% by weight of mineral oil and about 8.4% by weight of KRATON G1651, an eleven-to-one ratio, results in a gel having about the same firmness as a gel made from a slurry that is not degassed and that is composed of about ninety percent (90%) by weight of mineral oil and about ten percent (10%) by weight of KRATON G1651, a nine-to-one ratio.

Mineral oil is of a lighter density than KRATON and the two components will separate after mixing, with the lighter mineral oil rising to the top of the container. This separation may occur when attempting to form static slurry into gel over a period of several hours. The separation can cause the resulting gel to have a higher concentration of mineral oil at the top and a lower concentration at the bottom, e.g., a non-homogeneous gel. The speed of separation is a function of the depth or head height of the slurry being heated. The mass of slurry combined with the head height, the temperature at which the gel sets and the speed with which the energy can be transferred to the gel, factor into the determination or result of homogeneous gel versus a non-homogeneous gel.

The gel pad or gel cap in various aspects of the present invention may be gamma sterilized. The relative or comparative simplicity of qualifying the sterilization process, for example of gamma versus ethylene oxide, of the gel pad and the device with the gel pad is desirable. However, under gamma sterilization large bubbles can form in the gel pad causing potential cosmetic or aesthetic issues in the sterilized devices. The bubbles are more than ninety-nine percent (99%) room air, so removal of the dissolved air in the slurry is performed prior to forming the slurry into gel. For example, the slurry may be degassed via vacuum, as described above, and turned into gel by heat. Bubbles may still form in the gel during gamma sterilization but disappear in a period of about twenty-four (24) to seventy-two (72) hours. In one aspect, the percentage of dissolved gas in the mineral oil at room temperature is about ten percent (10%). The removal of the air in the gel has an additional effect of making the gel firmer. This however is counterbalanced by the softening effect on the gel caused by gamma radiation during gamma sterilization.

If the gel pad is to be gamma sterilized, the gel may include about ninety percent (90%) mineral oil by weight and about ten percent (10%) KRATON by weight. As stated above, degassing the slurry has the effect of making the gel firmer. However, the gamma radiation softens the gel to substantially the same firmness as a gel having about ninety percent (90%) mineral oil by weight and about ten percent (10%) KRATON by weight that is not degassed and gamma sterilized.

In one aspect, cyanoacrylate, e.g., SUPERGLUE or KRAZY GLUE, may be used to bond or otherwise couple or attach the gel pad 204 to the cap ring 202. The glue may attach to either the rubber or styrene component of the tri-block and the bond is frequently stronger than the gel material itself. In another aspect, a solvent may be used to dissolve the plastics in the cap ring and the polystyrene in the gel. The solution of solvent is applied to the gel pad and cap ring in either a spray or dip form. In effect, the solution melts both the plastic of the cap ring as well as the polystyrene in the gel pad to allow a chemical bond to form between the two, which remains when the solvent evaporates.

Polyethylene can be dissolved in mineral oil and then applied to the gel pad. The mineral oil will not evaporate but will over time absorb into the gel pad and impart a polyethylene layer on the gel pad that may have some beneficial properties.

In one aspect, the gel pad 204 is cast into a DYNAFLEX or KRATON polymer support structure, e.g., the cap ring 202. By using KRATON polymer or a similar material in the cap ring, ring adhesion between the gel pad 204 and the cap ring 202 can be achieved. The polystyrene in the gel is identified as achieving adhesion with polyphenylene oxide (PPO), polystyrene and other polymers.

In the casting process the gel pad 204 and the cap ring 202 are heated to a temperature above about 130° C. and held at that temperature for several hours, e.g., about three (3) to four (4) hours. The temperature used is not sufficient to deform the cap ring 202.

As stated above, in one aspect the cap ring 202 includes a polymer, e.g., polyethylene (PE). The gel includes mineral oil. PE has a higher molecular weight than mineral oil. PE is dissolved by mineral oil at high temperatures. As such, as the PE and the mineral oil in the gel pad 204 intermix as both are heated to and held at temperatures above about 130° C., a bond between the PE and gel pad is formed.

In one aspect, the cap ring 202 includes polycarbonate. The polycarbonate of the cap ring 202 does not form bonds with the gel pad 204 at 130° C. However, by raising the temperature to about 150° C. for a few minutes during casting, bonding occurs between the gel pad 204 and the cap ring 202. As such, heating the gel pad 204 and cap ring 202 to temperatures at which both the polystyrene of the gel and the polycarbonate are simultaneously beyond their melt points allow bonds to form between the gel pad and the cap ring. Alternatively, the gel pad 204 and cap ring 202 may be heated to near or at the glass transition temperature of the polycarbonate cap ring to form the bond between the gel pad and the cap ring.

In one aspect, casting the gel pad 204 into the cap ring 202 to form a gel cap 200 includes placing the cap ring into a mold cavity of a casting mold. The mold cavity may include support for the annular walls of the cap ring 202. The mold may be made of aluminum, copper, brass, or other mold material having good heat dissipation properties. However, those familiar with the art will recognize that other mold materials having lower heat dissipation properties will produce acceptable parts and these are contemplated as within the scope of the present invention as well.

The mold cavity having the cap ring 202 is filled with the slurry such that the slurry is in contact with the cap ring. To facilitate filling voids in the mold cavity with the slurry, the slurry may be preheated, for example, to about 52° C. (125° F.). Preheating the slurry to a temperature below the MGT reduces the viscosity of the slurry and allows the slurry to flow more easily. As stated above, the slurry may have been degassed in a vacuum. The slurry may be degassed again within the mold after the mold cavity is filled to remove air that may have been introduced during the filling of the mold cavity and to facilitate flow of the slurry into voids in the mold. Heat is applied to the mold having the cap ring 202 and the slurry, such as in an oven, until the slurry attains a temperature of about 150° C. As stated above, the slurry turns into gel at about 120° C., however, at about 150° C., the gel can bond to a polycarbonate cap ring 202. Depending on the material used to fabricate the cap ring 202, bonding may take place at temperatures other than about 150° C. If the cap ring 202 is fabricated of a material having a lower melting point than 120° C., then the gel pad 204, such as a gel slug 204, may be molded separately and then bonded to the cap ring. The slits 228, 230 may be molded into the gel pad 204 through the use of an insert in the form of the slit in the mold.

Once the temperature of the gel pad 204 reaches about 150° C., the gel cap 200 may be cooled, such as by air-cooling, cold-water immersion, or other cooling means that are well known in the art. At 150° C. the gel pad is soft and if it were distorted during cooling it would set with the distortion included. To reduce the likelihood of distorting the gel pad 204, the gel cap 200 may be cooled within the mold. Cooling times may vary based on parameters including size and configuration of the mold, quantity of gel, temperature and quantity of cooling medium, cooling medium properties and the mold material. As an example, the cooling time may be about two (2) hours if cooling in air and about fifteen (15) minutes if cooling in water. Whether cooling with air or water, the final properties of the gel are substantially the same. The gel cap 200 is typically cooled to about ambient room temperature, but may be cooled to lower temperatures. If the gel cap 200 is cooled to the freezing point of the gel, about 0° C., then the gel will freeze and become hard. This may be beneficial for other means of coupling the gel pad 204 to the cap ring 202, such as with a secondary operation. The gel cap 200 may be removed from the mold at any time after the gel has set.

When removed from the mold, the gel pad 204 typically has a tacky surface. The gel cap 200 may be coated with a powder, such as cornstarch, to substantially reduce or eliminate the tackiness of the cured gel pad 204.

As stated above, in another aspect, the gel pad 204 may be molded separately from the cap ring 202 and coupled to the cap ring by a secondary operation, such as by bonding. In one aspect, the gel pad 204 may be molded into a gel slug 204 having an outer perimeter smaller than the inner cylindrical wall of the cap ring 202 and to a height higher that the height of the cap ring. Since the gel pad 204 is being molded separate from the cap ring 202, the slurry only needs to be heated until it reaches about 120° C. and completes the transformation from slurry into gel and the gel becomes substantially transparent. The gel slug 204 may then be placed within the inner cylindrical wall of the cap ring 202. The gel slug 204 may be cooled and/or frozen prior to placing it within the inner cylindrical wall of the cap ring 202. The gel slug 204 may be coupled to the cap ring 202 through compression molding with the gel slug being compressed longitudinally so that the outer perimeter of the gel slug expands and compresses against the inner cylindrical wall of the cap ring. The gel slug 204 and cap ring 202 are heated to a sufficient temperature for the polystyrene of the gel and the polymer of the cap ring to form bonds between the gel and the cap ring. Molding the gel slug 204 separately from the cap ring 202 and heat bonding the gel slug to the cap ring at a later time is especially useful when the cap ring is made of a material that has a lower melting temperature than the MGT. In such situations, the gel slug 204 can be molded first and heat bonded to the cap ring 202 without melting the cap ring.

An advantage associated with the modified surgical access device is it enables a surgeon to quickly retract and protectively line an abdominal wall incision while being able to easily accommodate variations in abdominal wall thickness between patients. In addition, the device effectively seals around the interior and exterior of the incision, and allows a sealing cap to be coupled to the device to seal the abdominal cavity and to enable a laparoscopic procedure to be performed.

Many alterations and modifications may be made by those having ordinary skill in the art without departing from the spirit and scope of the invention. For these reasons, the above description should not be construed as limiting the invention, but should be interpreted as merely exemplary of the embodiments.

The invention claimed is:

1. A gel cap adapted for being coupled to a wound retractor, the wound retractor having a substantially noncompliant outer ring adapted for juxtaposition with an outer surface of a biological body wall and for disposition relative to an incision in the body wall, an inner ring adapted for juxtaposition with an inner surface of the biological body wall and for disposition relative to the incision in the body wall, and a sleeve adapted to traverse the incision in the body wall, the sleeve coupling the outer ring to the inner ring, the wound retractor being adapted to retract and seal the incision, the gelcap comprising:

a cap ring including a substantially cylindrical ring having,
      a first, proximal portion,
      a second, distal portion, and
      a plurality of lips at a distal end of the distal portion of the cap ring, each of the lips curving radially inward from the wall of the distal portion of the cap ring and extending around a portion of the circumference of the cap ring; and a gel pad made of a gel material, the gel pad being coupled to the cap ring and positioned at the proximal portion of the cap ring, the gel pad including an access portion for providing a passage from external the body to a body cavity, the passage forming an instrument seal in the presence of an instrument inserted therethrough and a zero seal in the absence of an instrument inserted therethrough, wherein, the lips are configured to receive the outer ring of the wound retractor such that the outer ring is positioned between the lip and the gel pad, and the gel pad being adapted to be placed in juxtaposition with the incision.

2. The gel cap of claim 1, the proximal portion of the cap ring including a plurality of apertures distributed about the circumference of the cap ring, the apertures extending through the wall of the proximal portion of the cap ring.

3. The gel cap of claim 2, wherein the gel of the gel pad covers and fills the apertures.

4. The gel cap of claim 3, the gel in the apertures connecting the gel at an outer portion of the cap ring to the gel at an inner portion of the cap ring.

5. The gel cap of claim 1, the gel of the gel cap extending into the distal portion of the cap ring.

6. The gel cap of claim 5, wherein the distal portion of the cap ring is adapted to receive the outer ring of the wound retractor such that the outer ring of the wound retractor embeds into the gel pad at the distal portion of the cap ring and displaces the gel, thereby forming a seal between the gel pad and the outer ring and sleeve of the wound retractor.

7. The gel cap of claim 1, the access portion of the gel pad including a plurality of intersecting dead-end slits.

8. The gel cap of claim 1, the distal portion of the cap ring including three lips, the three lips being substantially equally spaced about the circumference of the distal portion of the cap ring.

9. The gel cap of claim 8, each of the three lips extending about 60° around the circumference of the cap ring.

10. The gel cap of claim 1, the distal portion of the cap ring including more than three lips, the more than three lips being substantially equally spaced about the circumference of the distal portion of the cap ring.

11. The gel cap of claim 1, the distal portion of the cap ring including two lips, the two lips being substantially diametrically opposed about the circumference of the distal portion of the cap ring and each of the two lips extending a sufficient distance around the circumference of the cap ring to facilitate adequate coupling of the gel cap to the outer ring of the wound retractor.

12. The gel cap of claim 1, the cap ring being made of a polymer.

13. The gel cap of claim 12, the cap ring being made of polyethylene.

14. The gel cap of claim 12, the cap ring being made of polycarbonate.

15. The gel cap of claim 1, wherein the gel pad covers and seals the entire opening in the cap ring.

16. The gel cap of claim 1, wherein the gel pad is adapted to cover substantially the entire wound opening.

17. A gel cap adapted for being coupled to a wound retractor, the wound retractor having a substantially noncompliant outer ring adapted for juxtaposition with an outer surface of a biological body wall and for disposition relative to an incision in the body wall, an inner ring adapted for juxtaposition with an inner surface of the biological body wall and for disposition relative to the incision in the body wall, and a sleeve adapted to traverse the incision in the body wall, the sleeve coupling the outer ring to the inner ring, the wound retractor being adapted to retract and seal the incision, the gelcap comprising:

a cap ring including a substantially cylindrical ring having,
a first, proximal portion,
a second, distal portion, and
a plurality of lips at a distal end of the distal portion of the cap ring, each of the lips curving radially inward from the wall of the distal portion of the cap ring and extending around a portion of the circumference of the cap ring; and a gel pad made of a gel material, the gel pad being coupled to the cap ring and positioned at the proximal portion of the cap ring and extending into the distal portion of the cap ring, the gel pad including an access portion for providing a passage from external the body to a body cavity, the passage forming an instrument seal in the presence of an instrument inserted therethrough and a zero seal in the absence of an instrument inserted therethrough, wherein, the lips are configured to receive the outer ring of the wound retractor such that the outer ring is positioned between the lip and the gel pad, the distal portion of the cap ring is adapted to receive the outer ring of the wound retractor such that the outer ring of the wound retractor embeds into the gel pad at the distal portion of the cap ring and displaces the gel, thereby forming a seal between the gel pad and the outer ring and sleeve of the wound retractor, and the gel pad being adapted to be placed in juxtaposition with the incision.

18. The gel cap of claim 17, the proximal portion of the cap ring including a plurality of apertures distributed about the circumference of the cap ring, the apertures extending through the wall of the proximal portion of the cap ring.

19. The gel cap of claim 18, wherein the gel of the gel pad fills and covers the apertures.

20. The gel cap of claim 19, the gel in the apertures connecting the gel at an outer portion of the cap ring to the gel at an inner portion of the cap ring.

* * * * *